(12) United States Patent
Shoji et al.

(10) Patent No.: US 8,816,018 B2
(45) Date of Patent: Aug. 26, 2014

(54) RESIN COMPOSITION COMPRISING A CYCLIC CARBODIIMIDE

(75) Inventors: Shinichiro Shoji, Iwakuni (JP); Hirotaka Suzuki, Iwakuni (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 13/128,309

(22) PCT Filed: Dec. 15, 2009

(86) PCT No.: PCT/JP2009/071193
§ 371 (c)(1),
(2), (4) Date: May 9, 2011

(87) PCT Pub. No.: WO2010/071213
PCT Pub. Date: Jun. 24, 2010

(65) Prior Publication Data
US 2011/0224385 A1    Sep. 15, 2011

(30) Foreign Application Priority Data

Dec. 15, 2008 (JP) ................................. 2008-318533
Dec. 15, 2008 (JP) ................................. 2008-318598
Dec. 26, 2008 (JP) ................................. 2008-331961

(51) Int. Cl.
| | | |
|---|---|---|
| *C08G 63/00* | (2006.01) | |
| *C08J 5/18* | (2006.01) | |
| *C08K 5/3442* | (2006.01) | |
| *C07D 273/08* | (2006.01) | |
| *C08L 67/04* | (2006.01) | |
| *C07D 515/10* | (2006.01) | |
| *C08G 63/91* | (2006.01) | |

(52) U.S. Cl.
CPC ................. *C07D 515/10* (2013.01); *C08J 5/18* (2013.01); *C08K 5/3442* (2013.01); *C08J 2367/04* (2013.01); *C07D 273/08* (2013.01); *C08L 2205/02* (2013.01); *C08L 67/04* (2013.01); *C08G 63/912* (2013.01)
USPC ........... 525/437; 525/410; 525/415; 525/450; 528/492

(58) Field of Classification Search
USPC .................. 525/410, 415, 450, 437; 528/492
See application file for complete search history.

(56) References Cited

U.S. PATENT DOCUMENTS

| | | | |
|---|---|---|---|
| 2008/0039579 A1* | 2/2008 | Kimura et al. | 524/556 |
| 2008/0161554 A1 | 7/2008 | Dai et al. | |
| 2009/0137748 A1 | 5/2009 | Tanaka et al. | |
| 2009/0318628 A1* | 12/2009 | Tanaka et al. | 525/419 |
| 2010/0093888 A1* | 4/2010 | Endo et al. | 523/124 |

FOREIGN PATENT DOCUMENTS

| | | | | |
|---|---|---|---|---|
| DE | 10004328 | * | 8/2001 | ........... C07D 257/12 |
| DE | 10004328 A1 | | 8/2001 | |
| EP | 2 053 091 A1 | | 4/2009 | |
| JP | 2005-002174 A | | 1/2005 | |
| JP | 2006-328284 A | | 12/2006 | |
| JP | 2008-050584 A | | 3/2008 | |
| JP | 2008-248028 A | | 10/2008 | |
| JP | 2008-248184 A | | 10/2008 | |
| WO | 2007/091427 A1 | | 8/2007 | |
| WO | 2008/010355 A1 | | 1/2008 | |
| WO | WO 2008/102919 | * | 8/2008 | ............. C08L 67/04 |

OTHER PUBLICATIONS

Ulrich, H.; Chemistry and Technology of Carbodiimides, 2007, p. 227-242 and p. 259-273.*
Japanese Office Action in corresponding Application No. 2010-543023 dated Jun. 5, 2013.
European Search Report issued Sep. 13, 2013, European Patent Application No. 09833515.1.

* cited by examiner

*Primary Examiner* — Robert Jones, Jr.
(74) *Attorney, Agent, or Firm* — Sughrue Mion, PLLC

(57) ABSTRACT

A resin composition which comprises a polyester and is free from a smell produced from a free isocyanate compound. The resin composition comprises a polyester (component A) whose end is modified and a compound including a cyclic structure having one carbodiimide group whose first nitrogen and second nitrogen are bonded together by a bond group (component B).

14 Claims, No Drawings

RESIN COMPOSITION COMPRISING A CYCLIC CARBODIIMIDE

CROSS REFERENCE TO RELATED APPLICTION

This application is a National Stage of International Application No. PCT/JP2009/071193 filed Dec. 15, 2009.

TECHNICAL FIELD

The present invention relates to a resin composition comprising a polyester and a cyclic carbodiimide.

BACKGROUND ART

It has already been proposed to use a carbodiimide compound as an end-sealing agent for a polymer compound having a terminal acid group such as a carboxyl group so as to suppress the hydrolysis of the polymer compound (Patent Documents 1 and 2). The carbodiimide compound used in this proposal is a linear carbodiimide compound.

When the linear carbodiimide compound is used as an end-sealing agent for a polymer compound, a compound having an isocyanate group is liberated by a reaction for bonding the linear carbodiimide compound to an end of a polyester to produce a smell peculiar to an isocyanate compound, thereby deteriorating work environment.

Patent Document 3 discloses a macrocyclic carbodiimide compound. Since this compound is produced as a highly diluted solution, the concentration of the macrocyclic carbodiimide compound is low, whereby it takes many days to react it with a polymer and therefore the utility of the macrocyclic carbodiimide compound as an end-sealing agent for polymers is low. Further, Patent Document 3 does not take into consideration the reduction of an isocyanate smell produced by the end-sealing of a polymer. This macrocyclic carbodiimide compound has a long chain, is readily decomposed at a high temperature and therefore is not suitable for use as an end-sealing agent for polymers having a high melting point such as polyesters.
(Patent Document 1) JP-A 2008-050584
(Patent Document 2) JP-A 2005-2174
(Patent Document 3) US-A 2008/0161554

DISCLOSURE OF THE INVENTION

It is an object of the present invention to provide a resin composition which comprises a polyester and is free from a smell produced from a free isocyanate compound.

The inventors of the present invention have conducted intensive studies on a carbodiimide compound which does not liberate an isocyanate compound even when it reacts with an end of a polyester.

As a result, they have found that a compound having only one carbodiimide group in one cyclic structure does not liberate an isocyanate compound even when it reacts with an end of a polyester. The present invention has been accomplished based on this finding.

That is, the present invention is a resin composition which comprises a polyester (component A) and a compound including a cyclic structure having one carbodiimide group whose first nitrogen and second nitrogen are bonded together by a bond group (component B). The present invention also includes a molded article of the composition. The present invention further includes a process for producing a resin composition, comprising melt kneading a polyester (component A) with a compound including a cyclic structure having one carbodiimide group whose first nitrogen and second nitrogen are bonded together by a bond group (component B).

BEST MODE FOR CARRYING OUT THE INVENTION

<Cyclic Carbodiimide Compound (Component B)>

In the present invention, the cyclic carbodiimide compound (component B) has a cyclic structure. The cyclic carbodiimide compound may have a plurality of cyclic structures.

The cyclic structure has one carbodiimide group (—N=C=N—) whose first nitrogen and second nitrogen are bonded together by a bond group. One cyclic structure has only one carbodiimide group. The number of atoms contained in the cyclic structure is preferably 8 to 50, more preferably 10 to 30, much more preferably 10 to 20, particularly preferably 10 to 15.

The number of atoms contained in the cyclic structure is the number of atoms directly constituting the cyclic structure. For example, in the case of a 8-membered ring, the number of atoms is 8 and in the case of a 50-membered ring, the number of atoms is 50. When the number of atoms contained in the cyclic structure is smaller than 8, the stability of the cyclic carbodiimide compound degrades, thereby making it difficult to store and use the cyclic carbodiimide compound. There is no particular upper limit to the number of members of the ring from the viewpoint of reactivity but it is difficult to synthesize a cyclic carbodiimide compound having more than 50 atoms and its cost may rise sharply. From this point of view, the number of atoms contained in the cyclic structure is preferably 10 to 30, more preferably 10 to 20, particularly preferably 10 to 15.

The molecular weight of the cyclic carbodiimide compound is preferably 100 to 1,000. When the molecular weight is lower than 100, the structural stability and volatility of the cyclic carbodiimide compound may become problematic. When the molecular weight is higher than 1,000, synthesis in a dilution system is required for the production of the cyclic carbodiimide, or the yield lowers, thereby causing a cost problem. From this point of view, the molecular weight of the cyclic carbodiimide compound is more preferably 100 to 750, much more preferably 250 to 750.

The cyclic structure is preferably represented by the following formula (1).

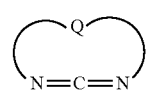

(1)

In the above formula, Q is a divalent to tetravalent bond group which is selected from an aliphatic group, an alicyclic group, an aromatic group or a combination of these and may contain a heteroatom or a substituent. Two of the valences of this bond group are used to form the cyclic structure. When Q is a tervalent or tetravalent bond group, it is bonded to a polymer or another cyclic structure by a single bond, a double bond, an atom or an atom group.

The bond group is preferably a divalent to tetravalent aliphatic group having 1 to 20 carbon atoms, a divalent to tetravalent alicyclic group having 3 to 20 carbon atoms, a divalent to tetravalent aromatic group having 5 to 15 carbon atoms, or a combination thereof. A bond group having a number of carbon atoms required for the formation of a cyclic structure is selected as the bond group. An example of the combination is an alkylene-arylene group in which an alkylene group and an arylene group are bonded together.

The aliphatic group, alicyclic group and aromatic group constituting the bond group may contain a heteroatom or a substituent. The heteroatom refers to O, N, S or P. Examples of the substituent include an alkyl group having 1 to 20 carbon atoms, aryl group having 6 to 15 carbon atoms, halogen atom, nitro group, amide group, hydroxyl group, ester group, ether group and aldehyde group.

In the present invention, examples of the halogen atom include chlorine atom, bromine atom and iodine atom.

The bond group (Q) is preferably a divalent to tetravalent bond group represented by the following formula (1-1), (1-2) or (1-3).

$$-Ar^1\text{-}(O\text{-}X^1)_s\text{-}O\text{-}Ar^2- \qquad (1\text{-}1)$$

$$-R^1\text{-}(O\text{-}X^2)_k\text{-}O\text{-}R^2- \qquad (1\text{-}2)$$

$$-X^3- \qquad (1\text{-}3)$$

In the above formulas, $Ar^1$ and $Ar^2$ are each independently a divalent to tetravalent aromatic group having 5 to 15 carbon atoms and may contain a heteroatom or a substituent.

Examples of the aromatic group include an arylene group having 5 to 15 carbon atoms, arenetriyl group having 5 to 15 carbon atoms, and arenetetrayl group having 5 to 15 carbon atoms. Examples of the arylene group (divalent) include phenylene group and naphthalenediyl group. Examples of the arenetriyl group (tervalent) include benzenetriyl group and naphthalenetriyl group. Examples of the arenetetrayl group (tetravalent) include benzenetetrayl group and naphthalenetetrayl group.

These aromatic groups may be substituted. Examples of the substituent include an alkyl group having 1 to 20 carbon atoms, aryl group having 6 to 15 carbon atoms, halogen atom, nitro group, amide group, hydroxyl group, ester group, ether group and aldehyde group. These aromatic groups may contain a heteroatom to form a heterocyclic structure. Examples of the heteroatom are O, N, S and P.

$R^1$ and $R^2$ are each independently a divalent to tetravalent aliphatic group having 1 to 20 carbon atoms, a divalent to tetravalent alicyclic group having 3 to 20 carbon atoms, a combination thereof, or a combination of the above aliphatic group, the above alicyclic group and a divalent to tetravalent aromatic group having 5 to 15 carbon atoms and may contain a heteroatom or a substituent.

Examples of the aliphatic group include an alkylene group having 1 to 20 carbon atoms, alkanetriyl group having 1 to 20 carbon atoms, and alkanetetrayl group having 1 to 20 carbon atoms. Examples of the alkylene group include methylene group, ethylene group, propylene group, butylenes group, pentylene group, hexylene group, heptylene group, octylene group, nonylene group, decylene group, dodecylene group and hexadecylene group. Examples of the alkanetriyl group include methanetriyl group, ethanetriyl group, propanetriyl group, butanetriyl group, pentanetriyl group, hexanetriyl group, heptanetriyl group, octanetriyl group, nonanetriyl group, decanetriyl group, dodecanetriyl group and hexadecanetriyl group. Examples of the alkanetetrayl group include methanetetrayl group, ethanetetrayl group, propanetetrayl group, butanetetrayl group, pentanetetrayl group, hexanetetrayl group, heptanetetrayl group, octanetetrayl group, nonanetetrayl group, decanetetrayl group, dodecanetetrayl group and hexadecanetetrayl group.

These aliphatic groups may be substituted. Examples of the substituent include an alkyl group having 1 to 20 carbon atoms, aryl group having 6 to 15 carbon atoms, halogen atom, nitro group, amide group, hydroxyl group, ester group, ether group and aldehyde group. These aliphatic groups may contain a heteroatom. Examples of the heteroatom are O, N, S and P.

Examples of the alicyclic group include a cycloalkylene group having 3 to 20 carbon atoms, cycloalkanetriyl group having 3 to 20 carbon atoms, and cycloalkanetetrayl group having 3 to 20 carbon atoms. Examples of the cycloalkylene group include cyclopropylene group, cyclobutylene group, cyclopentylene group, cyclohexylene group, cycloheptylene group, cyclooctylene group, cyclononylene group, cyclodecylene group, cyclododecylene group and cyclohexadecylene group. Examples of the cycloalkanetriyl group include cyclopropanetriyl group, cyclobutanetriyl group, cyclopentanetriyl group, cyclohexanetriyl group, cycloheptanetriyl group, cyclooctanetriyl group, cyclononanetriyl group, cyclodecanetriyl group, cyclododecanetriyl group and cyclohexadecanetriyl group. Examples of the cycloalkanetetrayl group include cyclopropanetetrayl group, cyclobutanetetrayl group, cyclopentanetetrayl group, cyclohexanetetrayl group, cycloheptanetetrayl group, cyclooctanetetrayl group, cyclononanetetrayl group, cyclodecanetetrayl group, cyclododecanetetrayl group and cyclohexadecanetetrayl group.

These alicyclic groups may be substituted. Examples of the substituent include an alkyl group having 1 to 20 carbon atoms, aryl group having 6 to 15 carbon atoms, halogen atom, nitro group, amide group, hydroxyl group, ester group, ether group and aldehyde group. These alicyclic groups may contain a heteroatom to form a heterocyclic structure. Examples of the heteroatom are O, N, S and P.

Examples of the aromatic group include an arylene group having 5 to 15 carbon atoms, arenetriyl group having 5 to 15 carbon atoms, and arenetetrayl group having 5 to 15 carbon atoms. Examples of the arylene group include phenylene group and naphthalenediyl group. Examples of the arenetriyl group (tervalent) include benzenetriyl group and naphthalenetriyl group. Examples of the arenetetrayl group (tetravalent) include benzenetetrayl group and naphthalenetetrayl group.

These aromatic groups may be substituted. Examples of the substituent include an alkyl group having 1 to 20 carbon atoms, aryl group having 6 to 15 carbon atoms, halogen atom, nitro group, amide group, hydroxyl group, ester group, ether group and aldehyde group.

These aromatic groups may contain a heteroatom to form a heterocyclic structure. Examples of the heteroatom are O, N, S and P.

$X^1$ and $X^2$ are each independently a divalent to tetravalent aliphatic group having 1 to 20 carbon atoms, a divalent to tetravalent alicyclic group having 3 to 20 carbon atoms, a divalent to tetravalent aromatic group having 5 to 15 carbon atoms or a combination thereof and may contain a heteroatom or a substituent.

Examples of the aliphatic group include an alkylene group having 1 to 20 carbon atoms, alkanetriyl group having 1 to 20 carbon atoms, and alkanetetrayl group having 1 to 20 carbon atoms. Examples of the alkylene group include methylene group, ethylene group, propylene group, butylene group, pentylene group, hexylene group, heptylene group, octylene group, nonylene group, decylene group, dodecylene group and hexadecylene group. Examples of the alkanetriyl group include methanetriyl group, ethanetriyl group, propanetriyl group, butanetriyl group, pentanetriyl group, hexanetriyl group, heptanetriyl group, octanetriyl group, nonanetriyl group, decanetriyl group, dodecanetriyl group and hexadecanetriyl group. Examples of the alkanetetrayl group include methanetetrayl group, ethanetetrayl group, propanetetrayl group, butanetetrayl group, pentanetetrayl group, hexanetetrayl group, heptanetetrayl group, octanetetrayl group, nonanetetrayl group, decanetetrayl group, dodecanetetrayl group and hexadecanetetrayl group.

These aliphatic groups may be substituted. Examples of the substituent include an alkyl group having 1 to 20 carbon atoms, aryl group having 6 to 15 carbon atoms, halogen atom, nitro group, amide group, hydroxyl group, ester group, ether group and aldehyde group. These aliphatic groups may contain a heteroatom. Examples of the heteroatom are O, N, S and P.

Examples of the alicyclic group include a cycloalkylene group having 3 to 20 carbon atoms, cycloalkanetriyl group having 3 to 20 carbon atoms, and cycloalkanetetrayl group having 3 to 20 carbon atoms. Examples of the cycloalkylene group include cyclopropylene group, cyclobutylene group, cyclopentylene group, cyclohexylene group, cycloheptylene group, cyclooctylene group, cyclononylene group, cyclodecylene group, cyclododecylene group and cyclohexadecylene group. Examples of the alkanetriyl group include cyclopropanetriyl group, cyclobutanetriyl group, cyclopentanetriyl group, cyclohexanetriyl group, cycloheptanetriyl group, cyclooctanetriyl group, cyclononanetriyl group, cyclodecanetriyl group, cyclododecanetriyl group and cyclohexadecanetriyl group. Examples of the alkanetetrayl group include cyclopropanetetrayl group, cyclobutanetetrayl group, cyclopentanetetrayl group, cyclohexanetetrayl group, cycloheptanetetrayl group, cyclooctanetetrayl group, cyclononanetetrayl group, cyclodecanetetrayl group, cyclododecanetetrayl group and cyclohexadecanetetrayl group.

These alicyclic groups may be substituted. Examples of the substituent include an alkyl group having 1 to 20 carbon atoms, aryl group having 6 to 15 carbon atoms, halogen atom, nitro group, amide group, hydroxyl group, ester group, ether group and aldehyde group. These alicyclic groups may contain a heteroatom to form a heterocyclic structure. Examples of the heteroatom are O, N, S and P.

Examples of the aromatic group include an arylene group having 5 to 15 carbon atoms, arenetriyl group having 5 to 15 carbon atoms, and arenetetrayl group having 5 to 15 carbon atoms. Examples of the arylene group include phenylene group and naphthalenediyl group. Examples of the arenetriyl group (tervalent) include benzenetriyl group and naphthalenetriyl group. Examples of the arenetetrayl group (tetravalent) include benzenetetrayl group and naphthalenetetrayl group.

These aromatic groups may be substituted. Examples of the substituent include an alkyl group having 1 to 20 carbon atoms, aryl group having 6 to 15 carbon atoms, halogen atom, nitro group, amide group, hydroxyl group, ester group, ether group and aldehyde group. These aromatic groups may contain a heteroatom to form a heterocyclic structure. Examples of the heteroatom are O, N, S and P.

s and k are each independently an integer of 0 to 10, preferably 0 to 3, more preferably 0 to 1. When s and k are larger than 10, it is difficult to synthesize the cyclic carbodiimide compound and its cost may rise sharply. From this point of view, the integer is preferably selected from 0 to 3. When s or k is 2 or more, $X^1$ or $X^2$ as a recurring unit may differ from another $X^1$ or $X^2$, respectively.

$X^3$ is a divalent to tetravalent aliphatic group having 1 to 20 carbon atoms, a divalent to tetravalent alicyclic group having 3 to 20 carbon atoms, a divalent to tetravalent aromatic group having 5 to 15 carbon atoms, or a combination thereof and may contain a heteroatom or a substituent.

Examples of the aliphatic group include an alkylene group having 1 to 20 carbon atoms, alkanetriyl group having 1 to 20 carbon atoms, and alkanetetrayl group having 1 to 20 carbon atoms. Examples of the alkylene group include methylene group, ethylene group, propylene group, butylene group, pentylene group, hexylene group, heptylene group, octylene group, nonylene group, decylene group, dodecylene group and hexadecylene group. Examples of the alkanetriyl group include methanetriyl group, ethanetriyl group, propanetriyl group, butanetriyl group, pentanetriyl group, hexanetriyl group, heptanetriyl group, octanetriyl group, nonanetriyl group, decanetriyl group, dodecanetriyl group and hexadecanetriyl group. Examples of the alkanetetrayl group include methanetetrayl group, ethanetetrayl group, propanetetrayl group, butanetetrayl group, pentanetetrayl group, hexanetetrayl group, heptanetetrayl group, octanetetrayl group, nonanetetrayl group, decanetetrayl group, dodecanetetrayl group and hexadecanetetrayl group.

These aliphatic groups may contain a substituent. Examples of the substituent include an alkyl group having 1 to 20 carbon atoms, aryl group having 6 to 15 carbon atoms, halogen atom, nitro group, amide group, hydroxyl group, ester group, ether group and aldehyde group. These aliphatic groups may contain a heteroatom. Examples of the heteroatom are O, N, S and P.

Examples of the alicyclic group include a cycloalkylene group having 3 to 20 carbon atoms, cycloalkanetriyl group having 3 to 20 carbon atoms, and cycloalkanetetrayl group having 3 to 20 carbon atoms. Examples of the cycloalkylene group include cyclopropylene group, cyclobutylene group, cyclopentylene group, cyclohexylene group, cycloheptylene group, cyclooctylene group, cyclononylene group, cyclodecylene group, cyclododecylene group and cyclohexadecylene group. Examples of the alkanetriyl group include cyclopropanetriyl group, cyclobutanetriyl group, cyclopentanetriyl group, cyclohexanetriyl group, cycloheptanetriyl group, cyclooctanetriyl group, cyclononanetriyl group, cyclodecanetriyl group, cyclododecanetriyl group and cyclohexadecanetriyl group. Examples of the alkanetetrayl group include cyclopropanetetrayl group, cyclobutanetetrayl group, cyclopentanetetrayl group, cyclohexanetetrayl group, cycloheptanetetrayl group, cyclooctanetetrayl group, cyclononanetetrayl group, cyclodecanetetrayl group, cyclododecanetetrayl group and cyclohexadecanetetrayl group.

These alicyclic groups may contain a substituent. Examples of the substituent include an alkyl group having 1 to 20 carbon atoms, arylene group having 6 to 15 carbon atoms, halogen atom, nitro group, amide group, hydroxyl group, ester group, ether group and aldehyde group. These alicyclic groups may contain a heteroatom to form a heterocyclic structure. Examples of the heteroatom are O, N, S and P.

Examples of the aromatic group include an arylene group having 5 to 15 carbon atoms, arenetriyl group having 5 to 15 carbon atoms, and arenetetrayl group having 5 to 15 carbon atoms. Examples of the arylene group include phenylene group and naphthalenediyl group. Examples of the arenetriyl group (tervalent) include benzenetriyl group and naphthalenetriyl group. Examples of the arenetetrayl group (tetravalent) include benzenetetrayl group and naphthalenetetrayl group.

These aromatic groups may be substituted. Examples of the substituent include an alkyl group having 1 to 20 carbon atoms, aryl group having 6 to 15 carbon atoms, halogen atom, nitro group, amide group, hydroxyl group, ester group, ether group and aldehyde group. These aromatic groups may contain a heteroatom to form a heterocyclic structure. Examples of the heteroatom are O, N, S and P.

As described above, $Ar^1$, $Ar^2$, $R^1$, $R^2$, $X^1$, $X^2$ and $X^3$ may contain a heteroatom.

When Q is a divalent bond group, all of $Ar^1$, $Ar^2$, $R^1$, $R^2$, $X^1$, $X^2$ and $X^3$ are divalent groups. When Q is a tervalent bond group, one of $Ar^1$, $Ar^2$, $R^1$, $R^2$, $X^1$, $X^2$ and $X^3$ is a tervalent group. When Q is a tetravalent bond group, one of $Ar^1$, $Ar^2$, $R^1$, $R^2$, $X^1$, $X^2$ and $X^3$ is a tetravalent group, or two of them are tervalent groups.

<Cyclic Carbodiimide (a)>

A compound represented by the following formula (2) (may be referred to as "cyclic carbodiimide (a)" hereinafter) can be given as the cyclic carbodiimide used in the present invention.

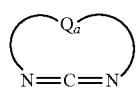
(2)

In the above formula, $Q_a$ is a divalent bond group which is selected from an aliphatic group, an alicyclic group, an aromatic group or a combination of these and may contain a heteroatom or a substituent.

The aliphatic group, alicyclic group and aromatic group are as defined in the above formula (1). In the compound of the formula (2), all of the aliphatic group, alicyclic group and aromatic group are divalent. $Q_a$ is preferably a divalent bond group of the following formula (2-1), (2-2) or (2-3).

(2-1)

(2-2)

(2-3)

In the above formulas, $Ar_a^1$, $Ar_a^2$, $R_a^1$, $R_a^2$, $X_a^1$, $X_a^2$, $X_a^3$, s and k are identical to $Ar^1$, $Ar^2$, $R^1$, $R^2$, $X^1$, $X^2$, $X^3$, s and k defined in the above formulas (1-1) to (1-3), respectively. However, all of them are divalent.

The cyclic carbodiimide (a) is preferably a compound represented by the following formula (2-1-1).

(2-1-1)

In the above formula, $X_a^1$ is an alkylene group having preferably 1 to 20 carbon atoms, more preferably 1 to 10 carbon atoms. Examples of the alkylene group include methylene group, ethylene group, trimethylene group and tetramethylene group.

In the above formula, $Ar_a^1$ and $Ar_a^2$ are each independently an arylene group having 5 to 15 carbon atoms which may be substituted. Examples of the arylene group include phenylene group and naphthalenediyl group. The substituent is an alkyl group having 1 to 20 carbon atoms, preferably 1 to 6 carbon atoms. Examples of the substituent include methyl group, ethyl group and propyl group.

The cyclic carbodiimide (a) is preferably a compound represented by the following formula (2-1-1a).

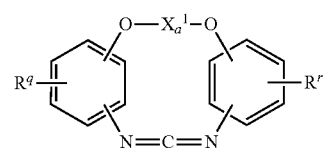
(2-1-1a)

In the above formula, $X_a^1$ is an alkylene group having preferably 1 to 20 carbon atoms, more preferably 1 to 10 carbon atoms, much more preferably 1 to 4 carbon atoms. Examples of the alkylene group include methylene group, ethylene group, trimethylene group and tetramethylene group.

In the above formula, $R^q$ and $R^r$ are each independently an alkyl group having preferably 1 to 20 carbon atoms, more preferably 1 to 6 carbon atoms, or hydrogen atom. Examples of the alkyl group include methyl group, ethyl group and propyl group.

The following compounds are enumerated as examples of the cyclic carbodiimide compound (a).

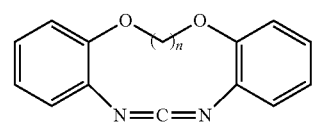

(n is an integer of 1 to 6)

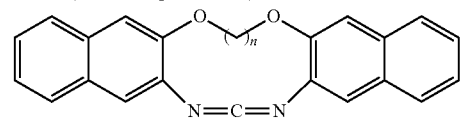

(n is an integer of 1 to 6)

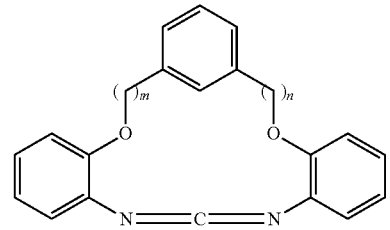

(m is an integer of 0 to 3, and n is an integer of 0 to 3)

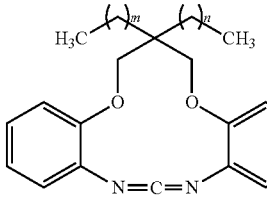

(m is an integer of 0 to 5, and n is an integer of 0 to 5)

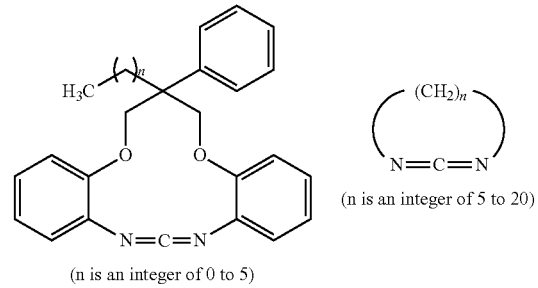

(n is an integer of 0 to 5)

(n is an integer of 5 to 20)

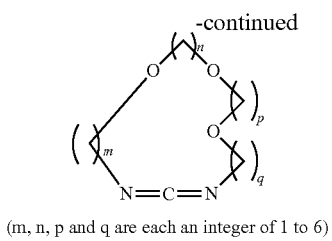

(m, n, p and q are each an integer of 1 to 6)

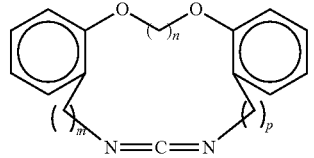

(m, n, p and q are each an integer of 1 to 6)

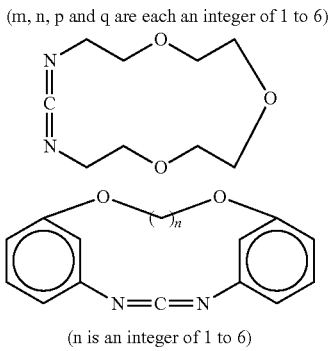

(n is an integer of 1 to 6)

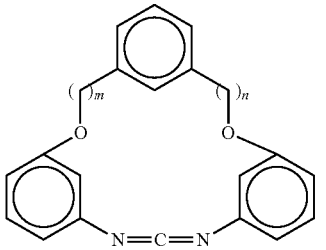

(m and n are each an integer of 0 to 3)

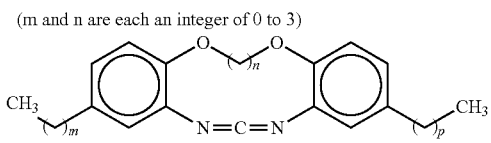

(m and p are each an integer of 1 to 5, and n is an integer of 1 to 6)

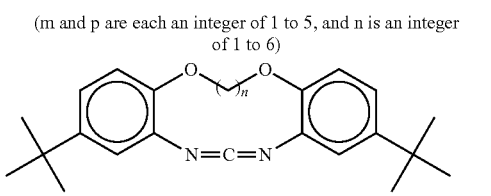

(n is an integer of 1 to 6)

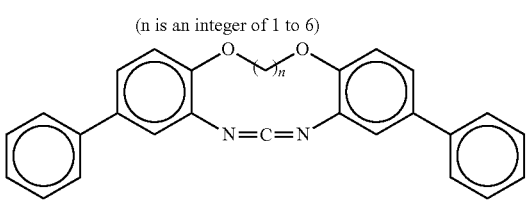

(n is an integer of 1 to 6)

<Cyclic Carbodiimide (b)>

Further, a compound represented by the following formula (3) (may be referred to as "cyclic carbodiimide (b)" hereinafter) can be given as the cyclic carbodiimide used in the present invention.

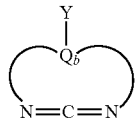

(3)

In the above formula, $Q_b$ is a tervalent bond group which is selected from an aliphatic group, an alicyclic group, an aromatic group or a combination of these and may contain a heteroatom or a substituent. Y is a carrier supporting the cyclic structure. The aliphatic group, alicyclic group and aromatic group are as defined in the formula (1). In the compound of the formula (3), one of the groups constituting $Q_b$ is tervalent.

$Q_b$ is preferably a tervalent bond group represented by the following formula (3-1), (3-2) or (3-3).

$$—Ar_b^1—(O—X_b^1)_s—O—Ar_b^2— \quad (3\text{-}1)$$

$$—R_b^1—(O—X_b^2)_k—O—R_b^2— \quad (3\text{-}2)$$

$$—X_b^3— \quad (3\text{-}3)$$

In the above formulas, $Ar_b^1$, $Ar_b^2$, $R_b^1$, $R_b^2$, $X_b^1$, $X_b^2$, $X_b^3$, s and k are identical to $Ar^1$, $Ar^2$, $R_1$, $R_2$, $X^1$, $X^2$, $X^3$ s and k defined in the above formulas (1-1) to (1-3), respectively. However, one of them is a tervalent group.

Y is preferably a single bond, a double bond, an atom, an atom group or a polymer. Y is a bond part, and a plurality of cyclic structures are bonded together by Y to form a structure represented by the formula (3).

The following compounds are enumerated as examples of the cyclic carbodiimide compound (b).

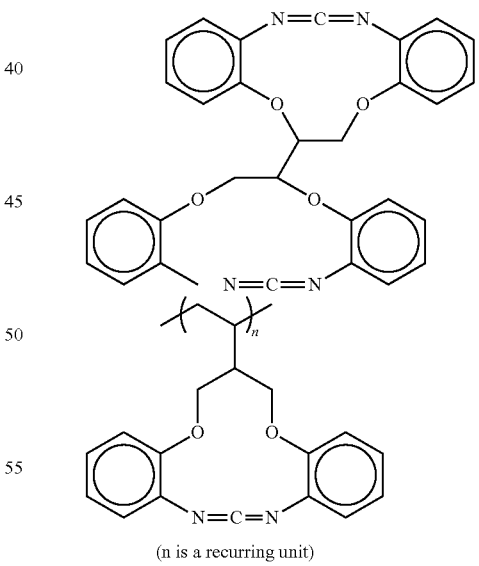

(n is a recurring unit)

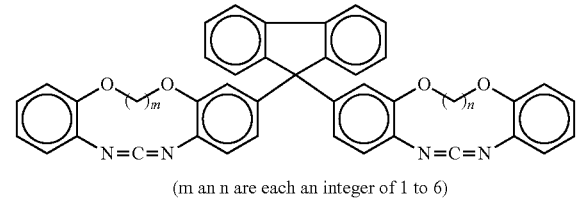

(m an n are each an integer of 1 to 6)

-continued

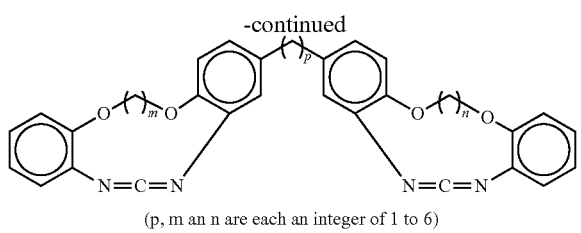

(p, m an n are each an integer of 1 to 6)

<Cyclic Carbodiimide (c)>

A compound represented by the following formula (4) (may be referred to as "cyclic carbodiimide (c)" hereinafter) can be given as the cyclic carbodiimide used in the present invention.

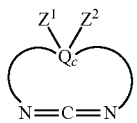

(4)

In the above formula, $Q_c$ is a tetravalent bond group which is selected from an aliphatic group, an alicyclic group, an aromatic group or a combination of these and may contain a heteroatom or a substituent. $Z^1$ and $Z^2$ are each a carrier supporting the cyclic structure. $Z^1$ and $Z^2$ may be bonded together to form a cyclic structure.

The aliphatic group, alicyclic group and aromatic group are as defined in the formula (1). In the compound of the formula (4), $Q_c$ is tetravalent. Therefore, one of these groups is tetravalent, or two of them are tervalent.

$Q_c$ is preferably a tetravalent bond group represented by the following formula (4-1), (4-2) or (4-3).

 (4-1)

 (4-2)

 (4-3)

$Ar_c^1$, $Ar_c^2$, $R_c^1$, $R_c^2$, $X_c^1$, $X_c^2$, $X_c^3$, s and k are identical to $Ar^1$, $Ar^2$, $R^1$, $R^2$, $X^1$, $X^2$, $X^3$, s and k defined in the above formulas (1-1) to (1-3), respectively. However, one of $Ar_c^1$, $Ar_c^2$, $R_c^1$, $R_c^2$, $X_c^1$, $X_c^2$ and $X_c^3$ is a tetravalent group, or two of them are tervalent groups.

Preferably, $Z^1$ and $Z^2$ are each independently a single bond, a double bond, an atom, an atom group or a polymer. $Z^1$ and $Z^2$ are each a bond part, and a plurality of cyclic structures are bonded together by $Z^1$ and $Z^2$ to form a structure represented by the formula (4).

The cyclic carbodiimide compound (c) is preferably a compound represented by the following formula (4-1-1).

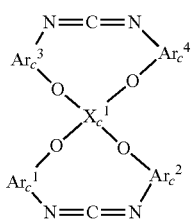

In the above formula, $X_c^1$ is an alkanetetrayl group having preferably 1 to 20 carbon atoms, more preferably 1 to 10 carbon atoms, much more preferably 1 to 6 carbon atoms. Examples of the alkanetetrayl group include isobutanetetrayl group, isopentanetetrayl group and neopentanetetrayl group. Out of these, a neopentanetetrayl group represented by the following formula is preferred.

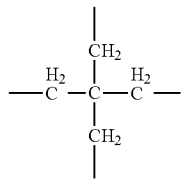

In the above formula, $Ar_c^1$, $Ar_c^2$, $Ar_c^3$ and $Ar_c^4$ are each independently an arylene group having 5 to 15 carbon atoms which may be substituted. Examples of the arylene group include phenylene group and naphthalenediyl group. The substituent is an alkyl group having 1 to 20 carbon atoms, preferably 1 to 6 carbon atoms. Examples of the substituent include methyl group, ethyl group and propyl group.

The cyclic carbodiimide (c) is preferably a compound represented by the following formula (2-1-1c).

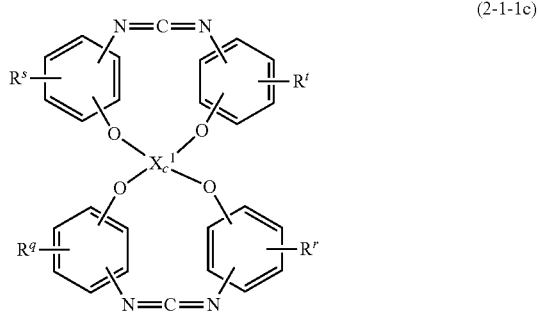

(2-1-1c)

In the above formula, $X_c^1$ is an alkanetetrayl group having preferably 1 to 20 carbon atoms, more preferably 1 to 10 carbon atoms, much more preferably 1 to 6 carbon atoms. Examples of the alkanetetrayl group include isobutanetetrayl group, isopentanetetrayl group and neopentanetetrayl group. Out of these, a neopentanetetrayl group represented by the following formula is preferred.

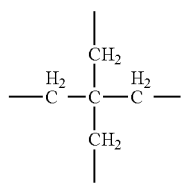

In the above formula, $R^q$, $R^r$, $R^s$ and $R^t$ are each independently an alkyl group having 1 to 20 carbon atoms, preferably 1 to 6 carbon atoms, or hydrogen atom. Examples of the alkyl group include methyl group, ethyl group and propyl group.

The following compounds are enumerated as examples of the cyclic carbodiimide compound (c).

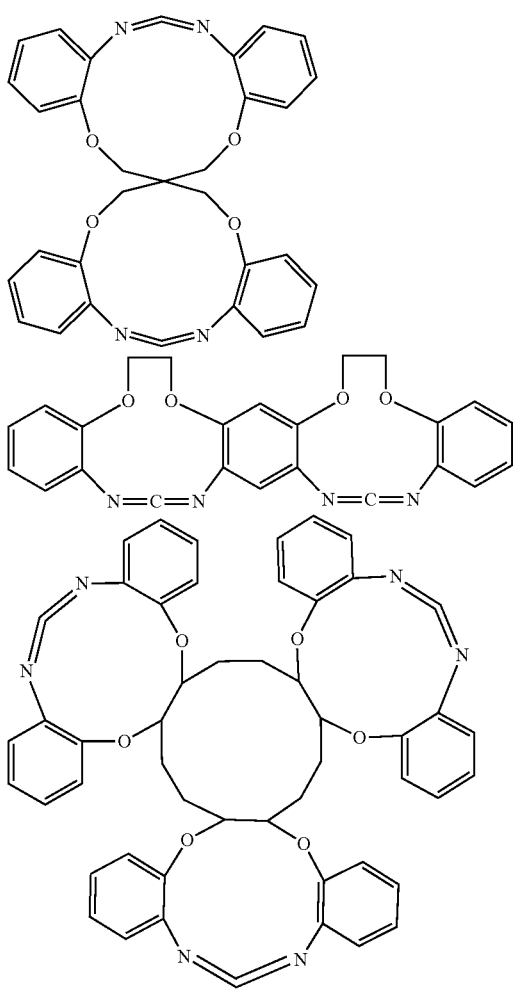

<Production Process of Cyclic Carbodiimide Compound>

As the process for producing the cyclic carbodiimide compound, a process for producing the compound from an amine compound through an isocyanate compound, a process for producing the compound from an amine compound through an isothiocyanate compound, a process for producing the compound from an amine compound through a triphenylphosphine compound, a process for producing the compound from an amine compound through an urea compound, a process for producing the compound from an amine compound through a thiourea compound, a process for producing the compound from a carboxylate compound through an isocyanate compound or a process for producing the compound by deriving a lactam compound may be employed.

(Production of Monocyclic Carbodiimide Compound (f))

The monocyclic carbodiimide compound (f) represented by the following formula (2-1-1) can be produced through the following steps (1) to (4).

(2-1-1)

(In the above formula, $Ar_a^1$ and $Ar_a^2$ are each independently an arylene group having 5 to 15 carbon atoms which may be substituted, and $X_a^1$ is an alkylene group having 1 to 20 carbon atoms.)

The step (1) is to obtain a nitro compound (c). The step (1) has step (1a) and step (1b). The step (2) is to obtain an amide compound (d) from the nitro compound (c). The step (3) and the step (4) are to obtain the monocyclic carbodiimide compound (f) from the amide compound (d). The step (3) to (4) has the embodiment of step (3a) through step (4a) and step (3b) through step (4b).

Stated more specifically, the carbodiimide compound (f) can be produced through the following schemes.
(scheme 1) step (1a)-step (2a)-step (3a)-step (4a)
(scheme 2) step (1a)-step (2a)-step (3b)-step (4b)
(scheme 3) step (1b)-step (2a)-step (3b)-step (4b)
(scheme 4) step (1b)-step (2a)-step (3a)-step (4a)
(step (1a))

The step (1a) is to obtain the nitro compound (c) of the following formula by reacting a compound of the following formula (a-1), a compound of the following formula (a-2) and a compound of the following formula (b-1).

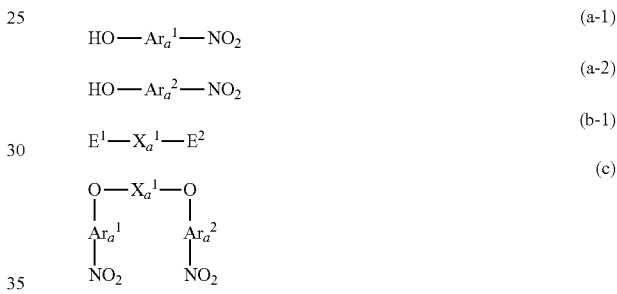

In the above formulas, $X_a^1$, $Ar_a^1$ and $Ar_a^2$ are as defined in the above formula (2-1-1).

$E^1$ and $E^2$ are each independently a group selected from the group consisting of halogen atom, toluenesulfonyloxy group, methanesulfonyloxy group, benzenesulfonyloxy group and p-bromobenzenesulfonyloxy group. Examples of the halogen atom include chlorine atom, bromine atom and iodine atom.

A conventionally known ether synthesizing method may be used for the reaction. For example, a Williamson's reaction in which a compound of the formula (a-1), a compound of the formula (a-2) and a compound of the formula (b-1) are reacted in a solvent in the presence of a basic compound may be used.

Sodium hydride, metal sodium, sodium hydroxide, potassium hydroxide or potassium carbonate is used as the basic compound. N,N-dimethylformamide, N-methyl-2-pyrrolidone or tetrahydrofuran is used as the solvent. The reaction temperature is preferably 25 to 150° C. Although the reaction proceeds swiftly under the above conditions, a phase-transfer catalyst may be added to promote the reaction.

(Step (1b))

The step (1b) is to obtain the nitro compound of the following formula (c) by reacting a compound of the following formula (a-i), a compound of the following formula (a-ii) and a compound of the following formula (b-i).

-continued

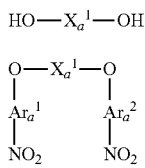
(b-i)

(c)

In the above formulas, $Ar_a^1$, $Ar_a^2$ and $X_a^1$ are as defined in the above formula (2-1-1). $E^3$ and $E^4$ are each independently a group selected from the group consisting of halogen atom, toluenesulfonyloxy group, methanesulfonyloxy group, benzenesulfonyloxy group and p-bromobenzenesulfonyloxy group.

A conventionally known ether synthesizing method may be used for the reaction. For example, a Williamson's reaction in which a compound of the formula (a-i), a compound of the formula (a-ii) and a compound of the formula (b-i) are reacted in a solvent in the presence of a basic compound may be used.

Sodium hydride, metal sodium, sodium hydroxide, potassium hydroxide or potassium carbonate is used as the basic compound. N,N-dimethylformamide, N-methyl-2-pyrrolidone or tetrahydrofuran is used as the solvent. The reaction temperature is preferably 25 to 150° C. Although the reaction proceeds under the above conditions, a phase-transfer catalyst is preferably added to promote the reaction. A tetrabutylammonium salt, trioctylmethylammonium salt, benzyldimethyloctadecylammonium salt or crown ether is used as the phase-transfer catalyst.

(Step (2a))

The step (2a) is to obtain the amine compound (d) of the following formula by reducing the obtained nitro compound (c).

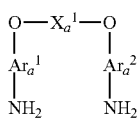
(d)

$Ar_a^1$, $Ar_a^2$ and $X_a^1$ are as defined in the above formula (2-1-1).

A conventionally known method may be used for the reaction. For example, the nitro compound (c) is catalytic reduced in a solvent in the presence of hydrogen and a catalyst.

Palladium carbon, palladium carbon-ethylenediamine complex, palladium-fibroin, palladium-polyethyleneimine, nickel or copper is used as the catalyst. Methanol, ethanol, isopropyl alcohol, dioxane, tetrahydrofuran, ethyl acetate, dichloromethane, chloroform or N,N-dimethylformamide is used as the solvent. The reaction temperature is preferably 25 to 100° C. Although the reaction proceeds at normal pressure, pressure is preferably applied to promote the reaction.

As another reaction for obtaining the amine compound (d), the nitro compound (c) is reacted with an acid and a metal, or the nitro compound (c) is reacted with hydrazine and a catalyst.

(Step (3a))

The step (3a) is to obtain a triphenylphosphine compound (e-1) of the following formula by reacting the obtained amine compound (d) with triphenylphosphine dibromide.

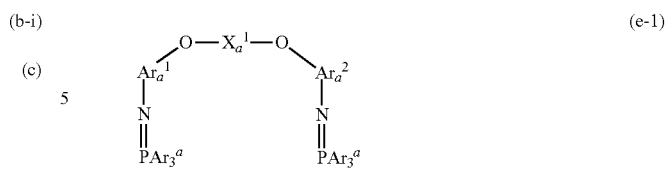
(e-1)

In the above formula, $Ar_a^1$, $Ar_a^2$ and $X_a^1$ are as defined in the above formula (2-1-1). $Ar^a$ is a phenyl group.

A conventionally known method may be used for the reaction. For example, the amine compound of the formula (d) is reacted with triphenylphosphine dibromide in a solvent in the presence of a basic compound. Triethylamine or pyridine is used as the basic compound. Dichloroethane, chloroform or benzene is used as the solvent. The reaction temperature is preferably 0 to 80° C.

(Step (4a))

The step (4a) is to obtain the cyclic carbodiimide compound (f) of the following formula by isocyanating the obtained triphenylphosphine compound in a reaction system and then decarbonating the isocyanated product directly.

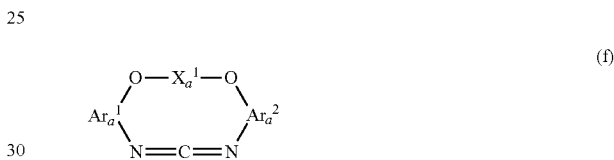
(f)

In the above formula, $Ar_a^1$, $Ar_a^2$ and $X_a^1$ are as defined in the above formula (2-1-1).

A conventionally known method may be used for the reaction. For example, the triphenylphosphine compound of the formula (e-1) is reacted in a solvent in the presence of di-tert-butyl dicarbonate and N,N-dimethyl-4-aminopyridine. Dichloromethane or chloroform is used as the solvent. The reaction temperature is preferably 10 to 40° C.

(Step (3b))

The step (3b) is to obtain an urea compound or thiourea compound of the following formula (e-2) by reacting the amine compound (d) with carbon dioxide or carbon disulfide.

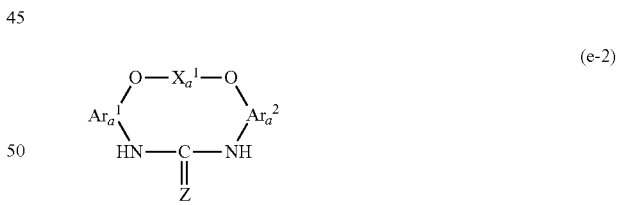
(e-2)

In the above formula, $Ar_a^1$, $Ar_a^2$ and $X_a^1$ are as defined in the above formula (2-1-1), and Z is an oxygen atom or sulfur atom.

A conventionally known method may be used for the reaction for obtaining the urea compound (e-2). For example, the amine compound (d) is reacted in a solvent in the presence of carbon dioxide, a phosphorus compound and a basic compound.

A phosphorous acid ester or a phosphonic acid ester is used as the phosphorus compound. Triethylamine, pyridine, imidazole or picoline is used as the basic compound. Pyridine, N,N-dimethylformamide, acetonitrile, chlorobenzene or toluene is used as the solvent. The reaction temperature is preferably 0 to 80° C.

As another reaction for obtaining the urea compound (e-2), the amine compound (d) is reacted with carbon monoxide, or the amine compound (d) is reacted with phosgene.

A conventionally known method may be used for the reaction for obtaining the thiourea compound (e-2). For example, the amine compound (d) is reacted in a solvent in the presence of carbon disulfide and a basic compound.

Triethylamine, pyridine, imidazole or picoline is used as the basic compound. Acetone, methanol, ethanol, isopropyl alcohol, 2-butanone, pyridine, N,N-dimethylformamide or acetonitrile is used as the solvent. The reaction temperature is preferably 25 to 90° C. Although the reaction proceeds swiftly under the above conditions, carbon tetrabromide may be used to promote the reaction.

(Step (4b))

The step (4b) is to obtain the cyclic carbodiimide compound (f) by dehydrating the obtained urea compound (e-2) or desulfurizing the thiourea compound (e-2).

A conventionally known method may be used for the reaction. For example, the urea compound (e-2) or the thiourea compound (e-2) is reacted in a solvent in the presence of toluenesulfonyl chloride or methylsulfonyl chloride to dehydrate the urea compound (e-2) or desulfurize the thiourea compound (e-2).

Dichloromethane, chloroform or pyridine is used as the solvent. The reaction temperature is preferably 0 to 80° C.

As another reaction for obtaining the cyclic carbodiimide compound (f), the urea compound (e-2) is reacted with mercury oxide, or the thiourea compound (e-2) is reacted with sodium hypochlorite.

<Production of Bicyclic Carbodiimide Compound (F)>

The bicyclic carbodiimide compound (F) represented by the following formula (4-1-1) can be produced through the following steps (1) to (4).

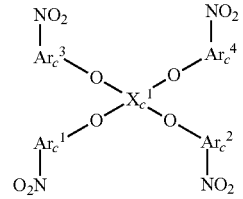

(4-1-1)

(In the above formula, $X_c^1$ is an alkanetetrayl group having 1 to 20 carbon atoms. $Ar_c^1$, $Ar_c^2$, $Ar_c^3$ and $Ar_c^4$ are each independently an arylene group having 5 to 15 carbon atoms which may be substituted.)

The step (1) is to obtain a nitro derivative (C). The step (1) has step (1A) and step (1B). The step (2) is to obtain an amide derivative (D) from the nitro derivative (C). The step (3) and the step (4) are to obtain the bicyclic carbodiimide compound (F) from the amide derivative (D). The step (3) to (4) has the embodiment of step (3A) through step (4A) and step (3B) through step (4B).

The carbodiimide compound (F) can be produced through the following schemes.
(scheme 1) step (1A)-step (2A)-step (3A)-step (4A)
(scheme 2) step (1A)-step (2A)-step (3B)-step (4B)
(scheme 3) step (1B)-step (2A)-step (3B)-step (4B)
(scheme 4) step (1B)-step (2A)-step (3A)-step (4A)

(Step (1A))

The step (1A) is to obtain the nitro compound (C) of the following formula by reacting compounds of the following formulas (A-1) to (A-4) and a compound of the following formula (B-1).

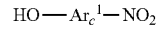 (A-1)

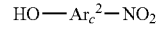 (A-2)

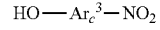 (A-3)

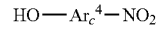 (A-4)

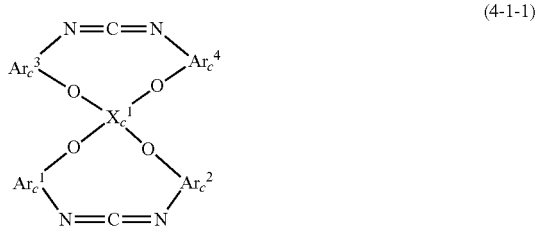 (B-1)

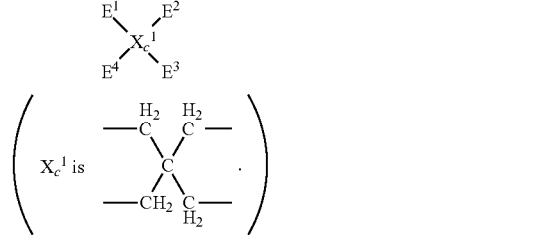 (C)

In the above formulas, $Ar_c^1$ to $Ar_c^4$ and $X_c^1$ are as defined in the formula (4-1-1). $E^1$ to $E^4$ are each independently a group selected from the group consisting of halogen atom, toluenesulfonyloxy group, methanesulfonyloxy group, benzenesulfonyloxy group and p-bromobenzenesulfonyloxy group. The reaction conditions are the same as those in the above step (1a).

(Step (1B))

The step (1B) is to obtain the nitro compound (C) of the following formula by reacting compounds of the following formulas (A-i) to (A-iv) and a compound of the following formula (B-i).

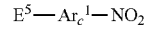 (A-i)

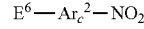 (A-ii)

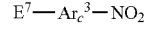 (A-iii)

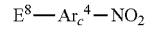 (A-iv)

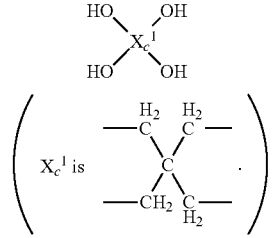 (B-i)

-continued

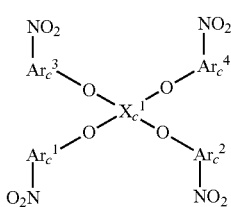
(C)

In the above formulas, $Ar_c^1$ to $Ar_c^4$ and $X_c^1$ are as defined in the formula (4-1-1). $E^5$ to $E^8$ are each independently a group selected from the group consisting of halogen atom, toluenesulfonyloxy group, methanesulfonyloxy group, benzenesulfonyloxy group and p-bromobenzenesulfonyloxy group.

The reaction conditions are the same as those in the above step (1b).

(Step (2A))

The step (2A) is to obtain the amine compound (D) of the following formula by reducing the obtained nitro compound.

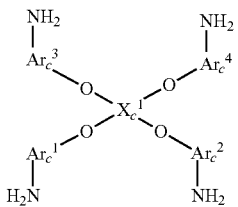
(D)

$Ar_c^1$ to $Ar_c^4$ and $X_c^1$ are as defined in the formula (4-1-1). The reaction conditions are the same as those in the above step (2a).

(Step (3A))

The step (3A) is to obtain a triphenylphosphine compound of the following formula (E-1) by reacting the obtained amine compound (D) with triphenylphosphine dibromide.

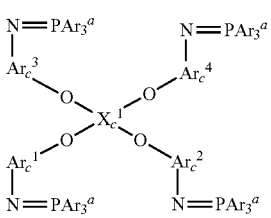
(E-1)

In the above formula, $Ar_c^1$ to $Ar_c^4$ and $X_c^1$ are as defined in the formula (4-1-1), and $Ar^a$ is a phenyl group. The reaction conditions are the same as those in the above step (3a).

(Step (4A))

The step (4A) is to obtain the compound (F) of the following formula by isocyanating the obtained triphenylphosphine compound in a reaction system and then decarbonating the isocyanated product directly.

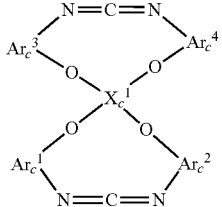
(F)

(In the above formula, $Ar_c^1$ to $Ar_c^4$ and $X_c^1$ are as defined in the formula (4-1-1).)

The reaction conditions are the same as those in the above step (4a).

(Step (3B))

The step (3B) is to obtain an urea compound or thiourea compound of the following formula (E-2) by reacting the amine compound with carbon dioxide or carbon disulfide.

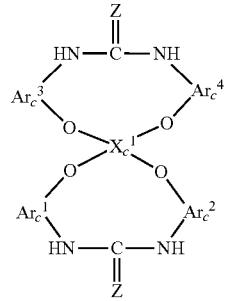
(E-2)

In the above formula, $Ar_c^1$ to $Ar_c^4$ and $X_c^1$ are as defined in the formula (4-1-1), and Z is an oxygen atom or sulfur atom. The reaction conditions are the same as those in the above step (3b).

(Step (4B))

The step (4B) is to obtain the compound (F) of the following formula by dehydrating the obtained urea compound or desulfurizing the thiourea compound.

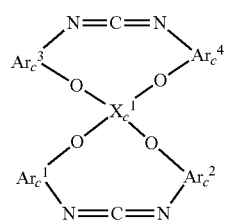
(F)

(In the above formula, $Ar_c^1$ to $Ar_c^4$ and $X_c^1$ are as defined in the formula (4-1-1).)

The reaction conditions are the same as those in the above step (4b).

Although the cyclic carbodiimide compound can seal the acid group of a polymer effectively, a conventionally known sealing agent for the carboxyl group of a polymer may be optionally used in combination as long as it does not work against the subject matter of the present invention. As the conventionally known carboxyl group sealing agent, agents disclosed by JP-A 2005-2174 such as epoxy compounds, oxazoline compounds and oxazine compounds may be used.

<Polyester (component A)>

In the present invention, the polyester (component A) is obtained by sealing at least part of an end of a polymer or copolymer prepared by polymerizing (a) a dicarboxylic acid or ester forming derivative and at least one selected from (b) a diol or ester forming derivative thereof, (c) a hydroxycarboxylic acid or ester forming derivative thereof and (d) a lactone with the component B.

Examples of the above dicarboxylic acid or ester forming derivative thereof (a) include aromatic dicarboxylic acids such as terephthalic acid, isophthalic acid, phthalic acid, 4,4'-diphenyldicarboxylic acid, 4,4'-benzophenonedicarboxylic acid, 4,4'-diphenoxyethanedicarboxylic acid, 4,4'-diphenylsulfonedicarboxylic acid, 2,6-naphthalenedicarboxylic acid, 1,6-naphthalenedicarboxylic acid, 2,7-naphthalenedicarboxylic acid, bis(4-carboxyphenyl)methane, anthracenedicarboxylic acid, 4,4'-diphenylether dicarboxylic acid, 5-tetrabutylphosphonium sulfoisophthalic acid and 5-sodium sulfoisophthalic acid or ester forming derivatives thereof. Aliphatic dicarboxylic acids such as oxalic acid, succinic acid, adipic acid, 1,6-hexanedicarboxylic acid and dimeric acid or ester forming derivatives thereof are also included. Alicyclic dicarboxylic acids such as cyclohexane-1,3-dicarboxylic acid, cyclohexane-1,4-dicarboxylic acid, decalin-2,6-dicarboxylic acid and tetralin-2,6-dicarboxylic acid or ester forming derivatives thereof are further included.

Examples of the above diol or ester forming derivative thereof (b) include aliphatic glycols having 2 to 20 carbon atoms such as ethylene glycol, diethylene glycol, 1,3-trimethylene glycol, 1,2-propylene glycol, 1,4-butanediol, neopentyl glycol, 1,5-pentanediol, 1,6-hexanediol, decamethylene glycol and dimer diol, and long-chain glycols having a molecular weight of 200 to 100,000, that is, aliphatic diol such as polyethylene glycol, polytrimethylene glycol, polypropylene-1,2-glycol and polytetramethylene glycol, or ester forming derivatives thereof. Alicyclic diols such as cyclohexane-1,2-diol, cyclohexane-1,4-diol and cyclohexane-1,4-dimethylol or ester forming derivatives thereof are also included. Aromatic dihydroxy compounds, that is, aromatic diols including an aromatic ring such as xylylene glycol, 4,4'-dihydroxybiphenyl, hydroquinone, tert-butyl hydroquinone, bisphenol A, bisphenol S and bisphenol F or ester forming derivatives thereof are further included.

The polyester (component A) is preferably a polyester whose main chain is essentially composed of a recurring unit represented by the following formula (II). At least part of an end of the component A is sealed with the component B.

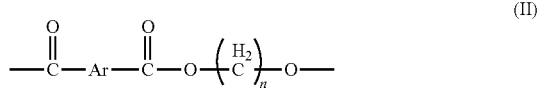
(II)

In the above formula, n is an integer of 2 to 4. Ar is preferably a phenylene group or naphthalenediyl group. Ar is particularly preferably a 1,4-phenylene group or 2,6-naphthalenediyl group.

The reduced viscosity of the polyester is preferably 0.2 to 1.5 dl/g, more preferably 0.3 to 1.3 dl/g.

Examples of the above hydroxycarboxylic acid or ester forming derivative thereof (c) include glycolic acid, D-lactic acid, L-lactic acid, racemic lactic acid, hydroxypropionic acid, 3-hydroxybutyric acid, hydroxyvaleric acid, hydroxycaproic acid, p-hydroxybenzoic acid, m-hydroxybenzoic acid, p-β-hydroxyethoxybenzoic acid, 6-hydroxy-2-naphthoic acid, oligo- or poly-caprolactone or ester forming derivatives thereof.

Out of the ester forming derivatives of the above hydroxycarboxylic acids, a lactone is preferably used for the production of the polyester. Examples of the lactone (d) include glycolide, D-lactide, L-lactide, meso-lactide, ε-caprolactone, δ-valerolactone, β-propiolactone, pivalolactone, β-benzylmalolactonate, γ-butyrolactone, 1,4-dioxan-2-one, undecalactone, 1,4-dioxepan-2-one, (R)-3-methyl-4-oxa-6-hexanolide and (S)-3-methyl-4-oxa-6-hexanolide. Monofunctional components such as stearyl alcohol, benzyl alcohol, stearic acid, benzoic acid, tert-butylbenzoic acid and benzoylbenzoic acid, and tri- or more functional components such as tricarballylic acid, trimellitic acid, trimesic acid, pyromellitic acid, gallic acid, trimethylolethane, trimethylolpropane, glycerol and pentaerythritol may also be used.

More specific examples of the polyester include polyglycolic acid, polylactic acid, poly(3-hydroxybutyric acid), poly(4-hydroxybutyric acid), poly(4-hydroxyvaleric acid), poly(3-hydroxyhexanoic acid) or aliphatic polyesters such as polycaprolactone, polyethylene adipate, polyethylene succinate, polybutylene adipate, polybutylene succinate polycyclohexanedimethanol and cyclohexane dicarboxylate, and aromatic polyesters such as polyethylene terephthalate, polybutylene terephthalate, polytrimethylene terephthalate, poly(1,4-methylolcyclohexane terephthalate), polyethylene 2,6-naphthalate, polybutylene 2,6-naphthalate and polytrimethylene 2,6-naphthalate. They may be used alone or in combination of two or more.

Polyesters obtained by any conventionally known production process may be used in the present invention as the polyester to be sealed with the component B. Out of these, polymers comprising a hydroxycarboxylic acid as the main constituent component are preferred, and polylactic acid is particularly preferred from the viewpoint of environmental preservation. Since polylactic acid is hydrolyzed more easily than other polyesters, its end is preferably sealed with the cyclic carbodiimide compound (component B). The polylactic acid includes stereocomplex polylactic acid which forms a stereocomplex crystal phase.

The main chain of the polylactic acid is essentially composed of a lactic acid unit represented by the following formula (I), and at least part of its end is sealed with the component B. In this text, the expression "essentially" means preferably 90 to 100 mol %, more preferably 95 to 100 mol %, much more preferably 98 to 100 mol %.

(I)

There are an L-lactic acid unit and a D-lactic acid unit which are optical isomers as the lactic acid unit represented by the formula (I). Preferably, the main chain of the polylactic acid is essentially composed of an L-lactic acid unit, a D-lactic acid unit or a combination thereof.

The polylactic acid is preferably poly(D-lactic acid) whose main chain is essentially composed of a D-lactic acid unit or poly(L-lactic acid) whose main chain is essentially composed of an L-lactic acid unit. The total amount of the other units constituting the main chain is preferably 0 to 10 mol %, more preferably 0 to 5 mol %, much more preferably 0 to 2 mol %.

The other units constituting the main chain include units derived from a dicarboxylic acid, a polyhydric alcohol, a hydroxycarboxylic acid and a lactone.

Examples of the dicarboxylic acid include succinic acid, adipic acid, azelaic acid, sebacic acid, terephthalic acid and isophthalic acid. Examples of the polyhydric alcohol include aliphatic polyhydric alcohols such as ethylene glycol, propylene glycol, butanediol, pentanediol, hexanediol, octanediol, glycerin, sorbitan, neopentyl glycol, diethylene glycol, triethylene glycol, polyethylene glycol and polypropylene glycol, and aromatic polyhydric alcohols such as an adduct of bisphenol with ethylene oxide. Examples of the hydroxycarboxylic acid include glycolic acid and hydroxybutyric acid. Examples of the lactone include glycolide, ε-caprolactone, β-propiolactone, δ-butyrolactone, β- or γ-butyrolactone, pivalolactone and δ-valerolactone.

The weight average molecular weight of the polylactic acid is preferably 100,000 to 500,000, more preferably 110,000 to 350,000, much more preferably 120,000 to 250,000 in order to achieve both of the mechanical properties and moldability of a molded article. The weight average molecular weight is a value which is measured by gel permeation chromatography (GPC) and calculated in terms of standard polystyrene.

When the polylactic acid (component A) is poly(D-lactic acid) or poly(L-lactic acid) and homo-phase polylactic acid, it has a crystal melting peak (Tmh) at 150 to 190° C. and a crystal melting heat (ΔHmsc) of not less than 10 J/g in differential scanning calorimeter (DSC) measurement. When the polylactic acid has the above crystal melting point and crystal melting heat, its heat resistance can be enhanced.

The main chain of the polylactic acid is preferably stereocomplex polylactic acid having a stereocomplex phase formed by the poly(L-lactic acid) unit and the poly(D-lactic acid) unit. The stereocomplex polylactic acid preferably shows a crystal melting peak at 190° C. or higher in differential scanning calorimeter (DSC) measurement.

Preferably, the stereocomplex polylactic acid has a stereo crystal rate (S) defined by the following equation (i) of 90 to 100%.

$$S=[\Delta Hms/(\Delta Hmh+\Delta Hms)]\times 100 \quad (i)$$

(ΔHms is the crystal melting enthalpy of stereocomplex-phase polylactic acid and ΔHmh is the melting enthalpy of the homo-phase crystal of polylactic acid.)

The stereocomplex polylactic acid preferably has crystallinity and more preferably has a stereo crystallization ratio (Sc) defined by the following equation (ii) based on the intensity ratio of diffraction peaks measured by wide-angle X-ray diffraction (XRD) of not less than 50%.

$$Sc(\%)=\Sigma I_{SCi}/(\Sigma I_{SCi}+I_{HM})\times 100 \quad (ii)$$

($\Sigma I_{SCi}=I_{SC1}+I_{SC2}+I_{SC3}$, $I_{SCi}$ (i=1 to 3) is the integral intensity of a diffraction peak at 2θ=12.0°, 20.7° or 24.0°, and $I_{HM}$ is an integral intensity ($I_{HM}$) of a diffraction peak derived from the homo-phase crystal which appears at 2 θ=16.5°.)

The stereo crystallization ratio (Sc) is preferably 50 to 100%, more preferably 60 to 95%, particularly preferably 65 to 90%. That is, when the polylactic acid has Sc within the above range, a molded article has preferred heat resistance and moist heat resistance.

The crystallinity degree, especially crystallinity degree measured by XRD of the stereocomplex polylactic acid is preferably at least 5%, more preferably 5 to 60%, much more preferably 7 to 50%, particularly preferably 10 to 45%.

The crystal melting point of the stereocomplex polylactic acid is preferably 190 to 250° C., more preferably 200 to 230° C. The crystal melting enthalpy measured by DSC of the stereocomplex polylactic acid is preferably not less than 20 J/g, more preferably 20 to 80 J/g, much more preferably 30 to 85 J/g. When the crystal melting point of the stereocomplex polylactic acid is lower than 190° C., heat resistance degrades. When the crystal melting point is higher than 250° C., the stereocomplex polylactic acid must be molded at a temperature higher than 250° C., whereby it may be difficult to suppress the thermal decomposition of the resin. Therefore, the resin composition of the present invention preferably shows a crystal melting peak at 190° C. or higher in differential scanning calorimeter (DSC) measurement.

The weight ratio of poly(D-lactic acid) to poly(L-lactic acid) in the stereocomplex polylactic acid is preferably 90/10 to 10/90. It is more preferably 80/20 to 20/80, much more preferably 30/70 to 70/30, particularly preferably 40/60 to 60/40. It is preferably as close to 1/1 as possible in theory.

The weight average molecular weight of the stereocomplex polylactic acid is preferably 100,000 to 500,000, more preferably 110,000 to 350,000, much more preferably 120,000 to 250,000. The weight average molecular weight is a value which is measured by gel permeation chromatography (GPC) and calculated in terms of standard polystyrene.

The poly(L-lactic acid) and the poly(D-lactic acid) can be produced by conventionally known methods. For example, poly(L-lactic acid) or poly(D-lactic acid) can be produced by ring-opening polymerizing L-lactide, and D-lactide in the presence of a metal-containing catalyst, respectively. Alternatively, they can be produced by solid-phase polymerizing low-molecular weight polylactic acid containing a metal-containing catalyst under reduced pressure or by increasing pressure from normal pressure in the presence or absence of an inert gas stream after it is optionally crystallized or without crystallizing it. Further, they can be produced by a direct polymerization process in which lactic acid is dehydrated and condensed in the presence or absence of an organic solvent.

The polymerization reaction can be carried out in conventionally known reactors. For example, in the ring-opening polymerization or direct polymerization process, vertical reactors or horizontal reactors equipped with a high-viscosity stirring blade such as a helical ribbon blade may be used alone or in combination. A batch, continuous or semi-batch system may be used, or a combination thereof may be used.

An alcohol may be used as a polymerization initiator. The alcohol preferably does not impede the polymerization of polylactic acid and is nonvolatile, as exemplified by decanol, dodecanol, tetradecanol, hexadecanol, octadecanol, ethylene glycol, trimethylolpropane and pentaerythritol. It can be said that it is preferred from the viewpoint of the prevention of the fusion of a resin pellet that a polylactic acid prepolymer used in the solid-phase polymerization process should be crystallized in advance. The prepolymer is polymerized in a solid state at a temperature equal to or higher than the glass transition temperature of the prepolymer and lower than the melting point in a fixed vertical or horizontal reactor or a rotary reactor (such as rotary kiln) whose vessel rotates, such as tumbler or kiln.

Examples of the metal-containing catalyst include alkali metals, alkali earth metals, rare earths, transition metals, and fatty acid salts, carbonates, sulfates, phosphates, oxides, hydroxides, halides and alcoholates of aluminum, germanium, tin, antimony and titanium. Out of these, the metal containing catalyst is preferably a fatty acid salt, carbonate, sulfate, phosphate, oxide, hydroxide, halide or alcoholate containing at least one metal selected from tin, aluminum, zinc, calcium, titanium, germanium, manganese, magnesium and rare earth elements.

Preferred examples of the catalyst include tin-containing compounds such as stannous chloride, stannous bromide, stannous iodide, stannous sulfate, stannic oxide, tin myristate, tin octylate, tin stearate and tetraphenyltin, in which a catalytic activity is low and a side-reaction hardly occurs. Out of these, tin (II) compounds, specifically diethoxytin, dinonyloxytin, tin (II) myristate, tin (II) octylate, tin (II) stearate and tin (II) chloride are particularly preferred.

The amount of the catalyst is $0.42\times10^{-4}$ to $100\times10^{-4}$ (mol), preferably $1.68\times10^{-4}$ to $42.1\times10^{-4}$ (mol), particularly preferably $2.53\times10^{-4}$ to $16.8\times10^{-4}$ (mol) based on 1 kg of lactide from the viewpoint of reactivity and the color and stability of the obtained polylactide.

It is preferred that the metal-containing catalyst used for the polymerization of the polylactic acid should be inactivated with a conventionally known deactivator prior to use of the polylactic acid. Examples of the deactivator include organic ligands consisting of chelate ligands which have an imino group and can coordinate to the polymerization metal catalyst.

Low oxidation number phosphoric acids having an acid number of 5 or less, such as dihydride oxophosphoric acid (I), dihydride tetraoxodiphosphoric acid (II, II), hydride trioxophosphoric acid (III), dihydride pentaoxodiphosphoric acid (III), hydride pentaoxodiphosphoric acid (II, IV), dodecaoxohexaphosphoric acid (III), hydride octaoxotriphosphoric acid (III, IV, IV), octaoxotriphosphoric acid (IV, III, IV), hydride hexaoxodiphosphoric acid (III, V), hexaoxodiphosphoric acid (IV), decaoxotetraphosphoric acid (IV), hendecaoxotetraphosphoric acid (IV) and enneaoxotriphosphoric acid (V, IV, IV) are also included.

Orthotriphosphoric acids represented by the formula $xH_2O.yP_2O_5$ and satisfying x/y=3; polyphosphoric acids called "diphosphoric acid, triphosphoric acid, tetraphosphoric acid and pentaphosphoric acid" according to the degree of condensation all of which satisfy 2>x/y>1 and mixtures thereof; metaphosphoric acids which satisfy x/y=1, particularly trimetaphosphoric acid and tetrametaphosphoric acid; ultraphosphoric acids having a net structure containing part of a phosphorus pentaoxide structure and satisfying 1>x/y>0 (may be collectively referred to as "metaphosphoric acid-based compounds"); acidic salts of these acids; partial esters and whole esters of monohydric or polyhydric alcohols of these acids or polyalkylene glycols; and phosphono-substituted lower aliphatic carboxylic acid derivatives of these acids are further included.

From the viewpoint of catalyst deactivation ability, orthophosphoric acids represented by the formula $xH_2O.yP_2O_5$ and satisfying x/y=3; polyphosphoric acids called "diphosphoric acid, triphosphoric acid, tetraphosphoric acid and pentaphosphoric acid" according to the degree of condensation and satisfying 2>x/y>1 and mixtures thereof; metaphosphoric acids satisfying x/y=1, particularly trimetaphosphoric acid and tetrametaphosphoric acid, ultraphosphoric acids having a net-like structure containing part of a phosphorus pentaoxide structure and satisfying 1>x/y>0 (may be collectively referred to as "metaphosphoric acid-based compounds"); acidic salts of these acids; and partial esters of monohydric or polyhydric alcohols of these acids or polyalkylene glycols are preferred.

The metaphosphoric acid-based compounds used in the present invention include cyclic metaphosphoric acids in which 3 to 200 phosphate units are condensed, ultra-region metaphosphoric acids having a solid net-like structure, and alkali metal salts; alkali earth metal salts and onium salts thereof. Out of these, cyclic sodium metaphosphate, ultraregion sodium metaphosphate and dihexylphosphonoethyl acetate (may be abbreviated as DHPA hereinafter) of a phosphono-substituted lower aliphatic carboxylic acid derivative are preferably used.

The lactide content of the polylactic acid is preferably 1 to 5,000 ppm by weight. Lactide contained in the polylactic acid deteriorates the resin at the time of melt processing, thereby worsening the color of the resin or making it unusable as a product as the case may be.

Although poly(L- and/or D-lactic acid) right after melt ring-opening polymerization generally contains 1 to 5 wt % of lactide, the content of lactide can be reduced to a preferred range in any stage between the end of polymerization of poly(L- and/or D-lactic acid) to the formation of polylactic acid by carrying out conventionally known lactide reduction methods, that is, vacuum volatilization with a single-screw or multi-screw extruder and high-vacuum treatment with a polymerizer alone or in combination.

As the lactide content becomes lower, the melt stability and moist heat stability of the resin improve more. However, since lactide reduces the melt viscosity of the resin, it is rational and economical to set the lactide content to a value suitable for a desired purpose. That is, it is rational to set the lactide content to 1 to 1,000 ppm by weight so as to achieve practical melt stability. It is more preferably 1 to 700 ppm by weight, much more preferably 2 to 500 ppm by weight, particularly preferably 5 to 100 ppm by weight. When the polylactic acid component has the above lactide content, the stability of the resin at the time of melt molding a molded article of the present invention is improved, the molded article can be produced efficiently, and the moist heat stability and low gas property of the molded article can be enhanced.

The stereocomplex polylactic acid can be obtained by bringing poly(L-lactic acid) and poly(D-lactic acid) into contact with each other in a weight ratio of 10/90 to 90/10, preferably melting and bringing them into contact with each other, more preferably melt kneading them together. The contact temperature is preferably 220 to 290° C., more preferably 220 to 280°, much more preferably 225 to 275° C. from the viewpoints of the improvement of the stability at the time of melting and the stereo crystallization ratio of the polylactic acid.

Although the melt kneading method is not particularly limited, a conventionally known batch or continuous type melt mixer is preferably used. For example, a melt stirring tank, single-screw or double-screw extruder, kneader, anaxial basket-type stirring tank (finisher), the Vibolac of Sumitomo Heavy Industries, Inc., the N-SCR of Mitsubishi Heavy Industries, Ltd., the spectacle blade, lattice blade or Kenix type stirrer of Hitachi, Ltd. or a tubular polymerizer equipped with a Sulzer SMLX type static mixer may be used. Out of these, an anaxial basket type stirring tank which is a self-cleaning type polymerizer, N-SCR and a double-screw extruder are preferred from the viewpoint of productivity and the quality, especially color of the polylactic acid.

The resin composition of the present invention contains an end-sealed polyester (component A) having a structure that the cyclic carbodiimide compound as the component B is bonded to an end of the polyester. The cyclic carbodiimide compound reacts with the carboxyl group of the polyester as follows to form the following structure at the end of the polyester.

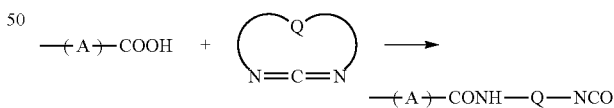

(A is the main chain of the polyester and Q is a bond group for bonding the first nitrogen and second nitrogen of the carbodiimide group.)

As will be described hereinafter, the resin composition of the present invention can be produced by mixing together the polyester and the cyclic carbodiimide compound (component B). The cyclic carbodiimide compound reacts with an end of the polyester to seal the end. The surplus cyclic carbodiimide compound remains unreacted in the resin composition.

Therefore, the resin composition of the present invention contains the polyester (component A) whose end has been sealed and the cyclic carbodiimide compound (component B). It may contain a polyester whose end is not sealed according to the degree of an end modification reaction.

The content of the cyclic carbodiimide compound (component B) which remains unreacted in the resin composition is 0.001 to 10 parts by weight, preferably 0.01 to 5 parts by weight, more preferably 0.1 to 1 part by weight based on 100 parts by weight of the polyester (component A).

<Production Process of Resin Composition>

The resin composition of the present invention can be produced by melt kneading together a polyester (component A) and a compound including a cyclic structure having one carbodiimide group whose first nitrogen and second nitrogen are bonded together by a bond group (component B).

When polylactic acid is used as the polyester, stereocomplex polylactic acid is formed and the resin composition of the present invention can be produced by mixing together poly(L-lactic acid) and poly(D-lactic acid) as the components A and a cyclic carbodiimide compound as the component B. The resin composition of the present invention can also be produced by mixing the cyclic carbodiimide compound (component B) after stereocomplex polylactic acid (component A) is formed by mixing together poly(L-lactic acid) and poly(D-lactic acid).

The method of adding and mixing the cyclic carbodiimide compound with the polyester is not particularly limited, and conventionally known methods such as one in which the cyclic carbodiimide compound is added as a solution, a melt or a master batch of a polymer for which it is used, or one in which a solid polymer is brought into contact with a liquid containing the cyclic carbodiimide compound dissolved therein, dispersed therein or molten therein to be impregnated with the cyclic carbodiimide compound may be used.

In the case of the method in which the cyclic carbodiimide compound is added as a solution, a melt or a master batch of a polyester for which it is used, a conventionally known kneader is used to add the cyclic carbodiimide compound. For kneading, the cyclic carbodiimide compound is preferably kneaded in a solution state or a molten state from the viewpoint of uniform kneading. The kneader is not particularly limited, and conventionally known vertical reactors, mixing tanks, kneading tanks, or single-screw or multi-screw horizontal kneaders such as single-screw or multi-screw extruders or kneaders are used. The time during which the cyclic carbodiimide compound is mixed with the polymer compound is not particularly specified and differs according to the mixer and the mixing temperature but 0.1 minute to 2 hours, preferably 0.2 to 60 minutes, more preferably 0.2 to 30 minutes.

As the solvent may be used a solvent which is inert to the polyester and the cyclic carbodiimide compound. A solvent which has affinity for both of them and dissolves at least part of each of them is particularly preferred.

The solvent is selected from a hydrocarbon-based solvent, a ketone-based solvent, an ester-based solvent, an ether-based solvent, a halogen-based solvent and an amide-based solvent.

Examples of the hydrocarbon-based solvent include hexane, cyclohexane, benzene, toluene, xylene, heptane and decane. Examples of the ketone-based solvent include acetone, methyl ethyl ketone, diethyl ketone, cyclohexanone and isophorone. Examples of the ester-based solvent include ethyl acetate, methyl acetate, ethyl succinate, methyl carbonate, ethyl benzoate and diethylene glycol diacetate. Examples of the ether-based solvent include diethyl ether, dibutyl ether, tetrahydrofuran, dioxane, diethylene glycol dimethyl ether, triethylene glycol diethyl ether and diphenyl ether. Examples of the halogen-based solvent include dichloromethane, chloroform, tetrachloromethane, dichloroethane, 1,1',2,2'-tetrachloroethane, chlorobenzene and dichlorobenzene. Examples of the amide-based solvent include formamide, N,N-dimethylformamide, N,N-dimethylacetamide and N-methyl-2-pyrrolidone. These solvents may be used alone or as a mixture.

In the present invention, the solvent is used in an amount of 1 to 1,000 parts by weight based on 100 parts by weight of the total of the polyester and the cyclic carbodiimide compound. When the amount of the solvent is smaller than 1 part by weight, there is no point in using the solvent. Although there is no upper limit to the amount of the solvent, it is about 1,000 parts by weight from the viewpoints of manipulation ease and reaction efficiency.

In the case of the method in which the solid polyester is brought into contact with a liquid containing the cyclic carbodiimide compound dissolved therein, dispersed therein or molten therein to be impregnated with the cyclic carbodiimide compound, the solid polyester is brought into contact with the cyclic carbodiimide compound dissolved in the above solvent, or the solid polylactic acid is brought into contact with an emulsion of the cyclic carbodiimide compound. To bring the solid polyester into contact with the cyclic carbodiimide compound, the polyester is immersed in the cyclic carbodiimide compound, or coated or sprayed with the cyclic carbodiimide compound.

A sealing reaction by the cyclic carbodiimide compound can be carried out at room temperature (25° C.) to 300° C. However, the reaction temperature is preferably 50 to 280° C., more preferably 100 to 280° C. from the viewpoint of reaction efficiency. Although the reaction proceeds more easily at a temperature at which the polyester is molten, the reaction is preferably carried out at a temperature lower than 300° C. to suppress the sublimation and decomposition of the cyclic carbodiimide compound. To reduce the melting temperature and increase the agitation efficiency of the polyester, use of the solvent is effective.

Although the reaction proceeds fully swiftly without a catalyst, a catalyst for promoting the reaction may be used. As the catalyst may be used conventional catalysts which are used for linear carbodiimide compounds. They may be used alone or in combination of two or more. The amount of the catalyst which is not particularly limited is preferably 0.001 to 1 part by weight, more preferably 0.01 to 0.1 part by weight, much more preferably 0.02 to 0.1 part by weight based on 100 parts by weight of the total of the polylactic acid and the cyclic carbodiimide.

As for the amount of the cyclic carbodiimide compound, the content of the carbodiimide group in the cyclic carbodiimide compound is selected from a range from 0.5 to 100 equivalents based on 1 equivalent of the acid group. When the content of the carbodiimide group is lower than 0.5 equivalent, there may be no point in using the carbodiimide. When the content is higher than 100 equivalents, the characteristic properties of a matrix may change. From this viewpoint of view, the content of the carbodiimide group is preferably 0.6 to 75 equivalents, more preferably 0.65 to 50 equivalents, much more preferably 0.7 to 30 equivalents, particularly preferably 0.7 to 20 equivalents based on the above standard.

<Stabilizer>

The resin composition of the present invention may contain a stabilizer. As the stabilizer may be used a stabilizer for ordinary thermoplastic resins. For example, an antioxidant agent and an optical stabilizer may be used. By mixing any one of them, a molded article having excellent mechanical properties, moldability, heat resistance and durability can be obtained.

The antioxidant is selected from a hindered phenol-based compound, a hindered amine-based compound, a phosphite-based compound and a thioether-based compound.

Examples of the hindered phenol-based compound include n-octadecyl-3-(3',5'-di-t-butyl-4'-hydroxyphenyl)-propionate, n-octadecyl-3-(3'-methyl-5'-t-butyl-4'-hydroxyphenyl)-propionate, n-tetradecyl-3-(3',5'-di-t-butyl-4'-hydroxyphenyl)-propionate, 1,6-hexanediol-bis[3-(3,5-di-t-butyl-4-hydroxyphenyl)-propionate], 1,4-butanediol-bis[3-(3,5-di-t-butyl-4-hydroxyphenyl)-propionate], 2,2'-methylene-bis(4-methyl-t-butylphenol), triethylene glycol-bis([3-(3-t-butyl-5-methyl-4-hydroxyphenyl)-propionate], tetrakis[methylene-3-(3',5'-di-t-butyl-4-hydroxyphenyl) propionate]methane and 3,9-bis[2-{3-(3-t-butyl-4-hydroxy-5-methylphenyl) propionyloxy}-1,1-dimethylethyl]2,4,8,10-tetraoxaspiro(5,5) undecane.

Examples of the hindered amine-based compound include N,N'-bis-3-(3',5'-di-t-butyl-4'hydroxyphenyl)propionylhexamethylenediamine, N,N'-tetramethylene-bis[3-(3'-methyl-5'-t-butyl-4'-hydroxyphenyl)propionyl]diamine, N,N'-bis[3-(3,5-di-t-butyl-4-hydroxyphenyl)-propionyl]hydrazine, N-salicyloyl-N'-salicylidenehydrazine, 3-(N-salicyloyl) amino-1,2,4-triazole and N,N'-bis[2-{3-(3,5-di-t-butyl-4-hydroxyphenyl) propionyloxy}ethyl]oxyamide. Triethylene glycol-bis[3-(3-t-butyl-5-methyl-4-hydroxyphenyl)-propionate] and tetrakis[methylene-3-(3',5'-di-t-butyl-4-hydroxyphenyl)propionate]methane are preferred.

The phosphite-based compound is preferably a compound having at least one P—O bond attached to an aromatic group, as exemplified by tris(2,6-di-t-butylphenyl)phosphite, tetrakis(2,6-di-t-butylphenyl)4,4'-biphenylene phosphite, bis(2,6-di-t-butyl-4-methylphenyl)pentaerythritol-di-phosphite, 2,2-methylenebis(4,6-di-t-butylphenyl)octylphosphite, 4,4'-butylidene-bis(3-methyl-6-t-butylphenyl-di-tridecyl)phosphite, 1,1,3-tris(2-methyl-4-ditridecylphosphite-5-t-butylphenyl)butane, tris(mixed mono- and di-nonylphenyl) phosphite, tris(nonylphenyl)phosphite and 4,4'-isopropylidenebis(phenyl-dialkylphosphite). Out of these, tris(2,6-di-t-butylphenyl)phosphite, 2,2-methylenebis(4,6-di-t-butylphenyl)octylphosphite, bis(2,6-di-t-butyl-4-methylphenyl)pentaerythritol-diphosphite and tetrakis(2,6-di-t-butylphenyl)-4,4'-biphenylene phosphite are preferably used.

Examples of the thioether-based compound include dilauryl thiodipropionate, ditridecyl thiodipropionate, dimyristyl thiodipropionate, distearyl thiodipropionate, pentaerythritol-tetrakis(3-laurylthiopropionate), pentaerythritol-tetrakis(3-dodecylthiopropionate), pentaerythritol-tetrakis(3-octadecylthiopropionate), pentaerythritol-tetrakis(3-myristylthiopropionate) and pentaerythritol-tetrakis(3-stearylthiopropionate).

The optical stabilizer is selected from a benzophenone-based compound, a benzotriazole-based compound, an aromatic benzoate-based compound, an anilide oxalate-based compound, a cyanoacrylate-based compound and a hindered amine-based compound.

Examples of the benzophenone-based compound include benzophenone, 2,4-dihydroxybenzophenone, 2,2'-dihydroxybenzophenone, 2,2',4,4'-tetrahydroxybenzophenone, 2-hydroxy-4-methoxybenzophenone, 2,2'-dihydroxy-4,4'-dimethoxybenzophenone, 2,2'-dihydroxy-4,4'-dimethoxy-5-sulfobenzophenone, 2-hydroxy-4-octoxybenzophenone, 2-hydroxy-4-dodecyloxybenzophenone, 2-hydroxy-4-octoxybenzophenone, 2-hydroxy-4-methoxy-5-sulfobenzophenone, 5-chloro-2-hydroxybenzophenone, 2-hydroxy-4-octoxybenzophenone, 2-hydroxy-4-methoxy-2'-carboxybenzophenone, and 2-hydroxy-4-(2-hydroxy-3-methyl-acryloxyisopropoxy) benzophenone.

Examples of the benzotriazole-based compound include 2-(5-methyl-2-hydroxyphenyl)benzotriazole, 2-(3,5-di-t-butyl-2-hydroxyphenyl)benzotriazole, 2-(3,5-di-t-amyl-2-hydroxyphenyl)benzotriazole, 2-(3',5'-di-t-butyl-4'-methyl-2'-hydroxyphenyl)benzotriazole, 2-(3,5-di-t-amyl-2-hydroxyphenyl)-5-chlorobenzotriazole, 2-(5-t-butyl-2-hydroxyphenyl)benzotriazole, 2-[2'-hydroxy-3',5'-bis(α,α-dimethylbenzyl)phenyl]benzotriazole, 2-[2'-hydroxy-3',5'-bis(α,α-dimethylbenzyl)phenyl]-2H-benzotriazole and 2-(4'-octoxy-2'-hydroxyphenyl)benzotriazole.

Examples of the aromatic benzoate-based compound include alkylphenyl salicylates such as p-t-butylphenyl salicylate and p-octylphenyl salicylate.

Examples of the anilide oxalate-based compound include 2-ethoxy-2'-ethyloxalic acid bisanilide, 2-ethoxy-5-t-butyl-2'-ethyloxalic acid bisanilide and 2-ethoxy-3'-dodecyloxalic acid bisanilide.

Examples of the cyanoacrylate-based compound include ethyl-2-cyano-3,3'-diphenyl acrylate and 2-ethylhexyl-cyano-3,3'-diphenyl acrylate.

Examples of the hindered amine-based compound include 4-acetoxy-2,2,6,6-tetramethylpiperidine, 4-stearoyloxy-2,2,6,6-tetramethylpiperidine, 4-acryloyloxy-2,2,6,6-tetramethylpiperidine, 4-(phenylacetoxy)-2,2,6,6-tetramethylpiperidine, 4-benzoyloxy-2,2,6,6-tetramethylpiperidine, 4-methoxy-2,2,6,6-tetramethylpiperidine, 4-octadecyloxy-2,2,6,6-tetramethylpiperidine, 4-cyclohexyloxy-2,2,6,6-tetramethylpiperidine, 4-benzyloxy-2,2,6,6-tetramethylpiperidine, 4-phenoxy-2,2,6,6-tetramethylpiperidine, 4-(ethylcarbamoyloxy)-2,2,6,6-tetramethylpiperidine, 4-(cyclohexylcarbamoyloxy)-2,2,6,6-tetramethylpiperidine, 4-(phenylcarbamoyloxy)-2,2,6,6-tetramethylpiperidine, bis(2,2,6,6-tetramethyl-4-piperidyl)carbonate, bis(2,2,6,6-tetramethyl-4-piperidyl)oxalate, bis(2,2,6,6-tetramethyl-4-piperidyl)malonate, bis(2,2,6,6-tetramethyl-4-piperidyl)sebacate, bis(2,2,6,6-tetramethyl-4-piperidyl)adipate, bis(2,2,6,6-tetramethyl-4-piperidyl)terephthalate, 1,2-bis(2,2,6,6-tetramethyl-4-piperidyloxy)-ethane, α,α'-bis(2,2,6,6-tetramethyl-4-piperidyloxy)-p-xylene, bis(2,2,6,6-tetramethyl-4-piperidyl)-tolylene-2,4-dicarbamate, bis(2,2,6,6-tetramethyl-4-piperidyl)-hexamethylene-1,6-dicarbamate, tris(2,2,6,6-tetramethyl-4-piperidyl)-benzene-1,3,5-tricarboxylate, tris(2,2,6,6-tetramethyl-4-piperidyl)-benzene-1,3,4-tricarboxylate, 1-[2-{3-(3,5-di-t-butyl-4-hydroxyphenyl)propionyloxy}-2,2,6,6-tetramethylpiperidine, and condensate of 1,2,3,4-butane tetracarboxylic acid, 1,2,2,6,6-pentamethyl-4-piperidinol and β,β,β',β'-tetramethyl-3,9-[2,4,8,10-tetraoxaspiro(5,5) undecane]dimethanol. In the present invention, the stabilizer components may be used alone or in combination of two or more.

Hindered phenol-based compounds and/or benzotriazole-based compounds are preferred as the stabilizer component. The content of the stabilizer is preferably 0.01 to 3 parts by weight, more preferably 0.03 to 2 parts by weight based on 100 parts by weight of the polyester (component A).

<Crystallization Accelerator>

The resin composition of the present invention may contain an organic or inorganic crystallization accelerator. When the resin composition contains the crystallization accelerator, a molded article having excellent mechanical properties, heat resistance and moldability can be obtained.

That is, by using the crystallization accelerator, a molded article which has improved moldability and crystallinity, is fully crystallized even by ordinary injection molding and has excellent heat resistance and moist heat stability can be obtained. In addition, the time required for the manufacture of a molded product can be drastically shortened and its economical effect is large.

A crystal nucleating agent which is generally used for crystalline resins may be used as the crystallization accelerator used in the present invention. Both an inorganic crystal nucleating agent and an organic crystal nucleating agent may be used.

Examples of the inorganic crystal nucleating agent include talc, kaolin, silica, synthetic mica, clay, zeolite, graphite, carbon black, zinc oxide, magnesium oxide, titanium oxide, calcium carbonate, calcium sulfate, barium sulfate, calcium sulfide, boron nitride, montmorillonite, neodymium oxide, aluminum oxide and phenylphosphonate metal salts. These inorganic crystal nucleating agents are preferably treated with a dispersion aid to improve their dispersibility in the composition and their effects and dispersed to such an extent that their primary particle diameters become about 0.01 to 0.5 µm.

Examples of the organic crystal nucleating agent include organic carboxylic acid metal salts such as calcium benzoate, sodium benzoate, lithium benzoate, potassium benzoate, magnesium benzoate, barium benzoate, calcium oxalate, disodium terephthalate, dilithium terephthalate, dipotassium terephthalate, sodium laurate, potassium laurate, sodium myristate, potassium myristate, calcium myristate, barium myristate, sodium octacosanoate, calcium octacosanoate, sodium stearate, potassium stearate, lithium stearate, calcium stearate, magnesium stearate, barium stearate, sodium montanate, calcium montanate, sodium toluoylate, sodium salicylate, potassium salicylate, zinc salicylate, aluminum dibenzoate, sodium β-naphthoate, potassium β-naphthoate and sodium cyclohexanecarboxylate, and organic sulfonic acid metal salts such as sodium p-toluenesulfonate and sodium sulfoisophthalate.

Organic carboxylic acid amides such as stearic acid amide, ethylenebis lauric acid amide, palmitic acid amide, hydroxystearic acid amide, erucic acid amide and tris(t-butylamide) trimesate, low-density polyethylene, high-density polyethylene, polyisopropylene, polybutene, poly-4-methylpentene, poly-3-methylbutene-1, polyvinyl cycloalkane, polyvinyl trialkylsilane, high-melting point polylactic acid, sodium salt of an ethylene-acrylate copolymer, sodium salt of a styrene-maleic anhydride copolymer (so-called "ionomer"), benzylidene sorbitol and derivative thereof such as dibenzylidene sorbitol are also included.

Out of these, talc and at least one selected from organic carboxylic acid metal salts are preferably used. These crystallization accelerators may be used alone or in combination of two or more in the present invention.

The content of the crystallization accelerator is preferably 0.01 to 30 parts by weight, more preferably 0.05 to 20 parts by weight based on 100 parts by weight of the polyester (component A).

<Filler>

The resin composition of the present invention may contain an organic or inorganic filler. When the resin composition contains a filler component, a molded article having excellent mechanical properties, heat resistance and moldability can be obtained.

Examples of the organic filler include chip fillers such as rice husk chips, wooden chips, bean curd refuse, old paper crushed chips and apparel crushed chips, fibrous fillers such as plant fibers including cotton fibers, hemp fibers, bamboo fibers, wooden fibers, kenaf fibers, jute fibers, banana fibers and coconut fibers, pulp and cellulose fibers obtained from these fibers, animal fibers including silk, wool, Angora, cashmere and camel fibers, and synthetic fibers including polyester fibers, nylon fibers and acrylic fibers, and powdery fillers such as paper powders, wooden powders, cellulose powders, rice husk powders, fruit shell powders, chitin powders, chitosan powders, protein powders and starch powders. From the viewpoint of moldability, paper powders, wooden powders, bamboo powders, cellulose powders, kenaf powders, rice husk powders, fruit shell powders, chitin powders, chitosan powders, protein powders and starch powders are preferred, and paper powders, wooden powders, bamboo powders, cellulose powders and kenaf powders are more preferred. Paper powders and wooden powders are much more preferred. Paper powders are particularly preferred.

Organic fillers obtained from natural products may be used but organic fillers recycled from waste materials such as used paper, waste timber and used clothing may also be used.

Conifers such as yellow pine, cedar, cypress and fir, and broadleaf trees such as beech, chinquapin and eucalyptus are preferred as timber.

Paper powders preferably contain an adhesive, especially an emulsion-based adhesive such as vinyl acetate resin-based emulsion or acrylic resin-based emulsion which is generally used to process paper, or a hot melt adhesive such as polyvinyl alcohol-based adhesive or polyamide-based adhesive from the viewpoint of moldability.

In the present invention, the content of the organic filler is not particularly limited but preferably 1 to 300 parts by weight, more preferably 5 to 200 parts by weight, much more preferably 10 to 150 parts by weight, particularly preferably 15 to 100 parts by weight based on 100 parts by weight of the polyester (component A) from the viewpoints of moldability and heat resistance. When the content of the organic filler is lower than 1 part by weight, the effect of improving the moldability of the composition becomes small and when the content is higher than 300 parts by weight, it is difficult to disperse the filler uniformly, or the strength and appearance as well as moldability and heat resistance of the composition as a material may deteriorate disadvantageously.

The composition of the present invention preferably contains an inorganic filler. By mixing an inorganic filler, a composition having excellent mechanical properties, heat resistance and moldability can be obtained. The inorganic filler used in the present invention is a fibrous, lamellar or powdery filler which is generally used to reinforce an ordinary thermoplastic resin.

Examples of the inorganic filler include fibrous inorganic fillers such as carbon nanotubes, glass fibers, asbestos fibers, carbon fibers, graphite fibers, metal fibers, potassium titanate whiskers, aluminum borate whiskers, magnesium-based whiskers, silicon-based whiskers, wollastonite, imogolite, sepiolite, asbestos, slug fibers, zonolite, gypsum fibers, silica fibers, silica-alumina fibers, zirconia fibers, boron nitride fibers, silicon nitride fibers and boron fibers, and lamellar and particulate inorganic fillers such as lamellar silicates, lamellar silicates exchanged with an organic onium ion, glass flakes, non-swelling mica, graphite, metal foils, ceramic beads, talc, clay, mica, sericite, zeolite, bentonite, dolomite, kaolin, powdery silicic acid, feldspar powder, potassium titanate, sillas balloon, calcium carbonate, magnesium carbonate, barium sulfate, calcium oxide, aluminum oxide, titanium oxide, aluminum silicate, silicon oxide, gypsum, novaculite, dosonite and carbon nanoparticles including white clay fullerene.

The lamellar silicates include smectite-based clay minerals such as montmorillonite, beidellite, nontronite, saponite, hectorite and sauconite, clay minerals such as vermiculite, halocite, kanemite and kenyaite, and swelling micas such as Li type fluorine taeniolite, Na type fluorine taeniolite, Li type tetrasilicon fluorine mica, Na type tetrasilicon fluorine mica. They may be natural or synthetic. Out of these, smectite-based clay minerals such as montmorillonite and hectorite and swelling synthetic micas such as Li type fluorine taeniolite and Na type tetrasilicon fluorine mica are preferred.

Out of these inorganic fillers, fibrous or lamellar inorganic fillers are preferred, and glass fibers, wollastonite, aluminum borate whiskers, potassium titanate whiskers, mica, kaolin and cation exchanged lamellar silicates are particularly preferred. The aspect ratio of the fibrous filler is preferably 5 or more, more preferably 10 or more, much more preferably 20 or more.

The filler may be covered or bundled with a thermoplastic resin such as an ethylene-vinyl acetate copolymer or a thermosetting resin such as epoxy resin, or treated with a coupling agent such as aminosilane or epoxysilane.

The content of the inorganic filler is preferably 0.1 to 200 parts by weight, more preferably 0.5 to 100 parts by weight, much more preferably 1 to 50 parts by weight, particularly preferably 1 to 30 parts by weight, most preferably 1 to 20 parts by weight based on 100 parts by weight of the polyester (component A).

<Release Agent>

The resin composition of the present invention may contain a release agent. As the release agent used in the present invention may be used a release agent used for ordinary thermoplastic resins. The release agent is selected from fatty acid, fatty acid metal salt, oxyfatty acid, paraffin, low-molecular weight polyolefin, fatty acid amide, alkylenebis fatty acid amide, aliphatic ketone, fatty acid partially saponified ester, fatty acid lower alcohol ester, fatty acid polyhydric alcohol ester, fatty acid polyglycol ester and modified silicone. When the resin composition contains a release agent, a polylactic acid molded article having excellent mechanical properties, moldability and heat resistance can be obtained.

The fatty acid is preferably a fatty acid having 6 to 40 carbon atoms, as exemplified by oleic acid, stearic acid, lauric acid, hydroxystearic acid, behenic acid, arachidonic acid, linoleic acid, linolenic acid, ricinoleic acid, palmitic acid, montanic acid and mixtures thereof. The fatty acid metal salt is preferably an alkali metal salt or alkali earth metal salt of a fatty acid having 6 to 40 carbon atoms, as exemplified by calcium stearate, sodium montanate and calcium montanate.

Examples of the oxyfatty acid include 1,2-oxystearic acid. The paraffin is preferably a paraffin having 18 or more carbon atoms, as exemplified by liquid paraffin, natural paraffin, microcrystalline wax and petrolactam.

The low-molecular weight polyolefin is preferably a polyolefin having a molecular weight of 5,000 or less, as exemplified by polyethylene wax, maleic acid modified polyethylene wax, oxide type polyethylene wax, chlorinated polyethylene wax and polypropylene wax. The fatty acid amide is preferably a fatty acid amide having 6 or more carbon atoms, as exemplified by oleic acid amide, erucic acid amide and behenic acid amide.

The alkylenebis fatty acid amide is preferably an alkylenebis fatty acid amide having 6 or more carbon atoms, as exemplified by methylenebis stearic acid amide, ethylenebis stearic acid amide and N,N-bis(2-hydroxyethyl)stearic acid amide. The aliphatic ketone is preferably an aliphatic ketone having 6 or more carbon atoms, as exemplified by higher aliphatic ketones.

Examples of the fatty acid partially saponified ester include montanic acid partially saponified esters. Examples of the fatty acid lower alcohol ester include stearic acid esters, oleic acid esters, linoleic acid esters, linolenic acid esters, adipic acid esters, behenic acid esters, arachidonic acid esters, montanic acid esters and isostearic acid esters.

Examples of the fatty acid polyhydric alcohol ester include glycerol tristearate, glycerol distearate, glycerol monostearate, pentaerythritol tetrastearate, pentaerythritol tristearate, pentaerythritol distearate, pentaerythritol monostearate, pentaerythritol adipate stearate and sorbitan monobehenate. Examples of the fatty acid polyglycol ester include polyethylene glycol fatty acid esters and polypropylene glycol fatty acid esters.

Examples of the modified silicone include polyether modified silicone, higher fatty acid alkoxy modified silicone, higher fatty acid-containing silicone, higher fatty acid ester modified silicone, methacryl modified silicone and fluorine modified silicone.

Out of these, fatty acids, fatty acid metal salts, oxyfatty acids, fatty acid esters, fatty acid partially saponified esters, paraffins, low-molecular weight polyolefins, fatty acid amides and alkylenebis fatty acid amides are preferred, and fatty acid partially saponified esters and alkylenebis fatty acid amides are more preferred. Montanic acid esters, montanic acid partially saponified esters, polyethylene wax, acid value polyethylene wax, sorbitan fatty acid esters, erucic acid amide and ethylenebis stearic acid amide are much more preferred, and montanic acid partially saponified esters and ethylenebis stearic acid amide are particularly preferred.

These release agents may be used alone or in combination of two or more. The content of the release agent is preferably 0.01 to 3 parts by weight, more preferably 0.03 to 2 parts by weight based on 100 parts by weight of the polyester (component A).

<Antistatic Agent>

The resin composition of the present invention may contain an antistatic agent. Examples of the antistatic agent include quaternary ammonium salt-based and sulfonate-based compounds such as (β-lauramidepropionyl)trimethylammonium sulfate and sodium dodecylbenzenesulfonate, and alkyl phosphate-based compounds.

In the present invention, these antistatic agents may be used alone or in combination of two or more. The content of the antistatic agent is preferably 0.05 to 5 parts by weight, more preferably 0.1 to 5 parts by weight based on 100 parts by weight of the polyester (component A).

<Plasticizer>

The resin composition of the present invention may contain a plasticizer. Generally known plasticizers may be used as the platicizer. The plasticizer is selected from a polyester-based plasticizer, glycerin-based plasticizer, polycarboxylate-based plasticizer, phosphate-based plasticizer, polyalkylene glycol-based plasticizer and epoxy-based plasticizer.

Examples of the polyester-based plasticizer include polyesters comprising an acid component such as adipic acid, sebacic acid, terephthalic acid, isophthalic acid, naphthalenedicarboxylic acid or diphenyldicarboxylic acid and a diol component such as ethylene glycol, propylene glycol, 1,3-propanediol, 1,3-butanediol, 1,4-butanediol, 1,6-hexanediol or diethylene glycol, and polyesters comprising a hydroxycarboxylic acid such as polycaprolactone. The ends of these polyesters may be sealed with a monofunctional carboxylic acid or a monofunctional alcohol.

Examples of the glycerin-based plasticizer include glycerin monostearate, glycerin distearate, glycerin monoacetomonolaurate, glycerin monoacetomonostearate, glycerin diacetomonooleate and glycerin monoacetomonomontanate.

Examples of the polycarboxylate-based plasticizer include phthalic acid esters such as dimethyl phthalate, diethyl phthalate, dibutyl phthalate, diheptyl phthalate, dibenzyl phthalate and butylbenzyl phthalate, trimellitic acid esters such as tributyl trimellitate, trioctyl trimellitate and trihexyl trimellitate, adipic acid esters such as isodecyl adipate and n-decyl-n-octyl adipate, citric acid esters such as tributyl acetylcitrate, azelaic acid esters such as bis(2-ethylhexyl)azelate, and sebacic acid esters such as dibutyl sebacate and bis(2-ethylhexyl) sebacate.

Examples of the phosphate-based plasticizer include tributyl phosphate, tris(2-ethylhexyl)phosphate, trioctyl phosphate, triphenyl phosphate, tricresyl phosphate and diphenyl-2-ethylhexyl phosphate.

Examples of the polyalkylene glycol-based plasticizer include polyalkylene glycols such as polyethylene glycol, polypropylene glycol, polytetramethylene glycol, poly(ethylene oxide-propylene oxide) block and/or random copolymer, ethylene oxide addition polymer of a bisphenol and tetrahydrofuran addition polymer of a bisphenol, and terminal sealing compounds such as terminal epoxy modified compounds, terminal ester modified compounds and terminal ether modified compounds of these polyalkylene glycols.

Examples of the epoxy-based plasticizer include epoxy triglyceride comprising alkyl epoxystearate and soybean oil, and epoxy resin obtained from bisphenol A and epichlorohydrin.

Other examples of the plasticizer include benzoates of an aliphatic polyol such as neopentyl glycol dibenzoate, diethylene glycol dibenzoate and triethylene glycol-bis(2-ethylbutyrate), fatty acid amides such as stearic acid amide, fatty acid esters such as butyl oleate, oxyacid esters such as methyl acetyl ricinoleate and butyl acetyl ricinoleate, pentaerythritol, sorbitols, polyacrylates, silicone oil and paraffins.

The plasticizer is preferably at least one selected from polyester-based plasticizers and polyalkylene-based plasticizers. They may be used alone or in combination of two or more.

The content of the plasticizer is preferably 0.01 to 30 parts by weight, more preferably 0.05 to 20 parts by weight, much more preferably 0.1 to 10 parts by weight based on 100 parts by weight of the polyester (component A). In the present invention, a crystal nucleating agent and a plasticizer may be used independently but preferably in combination.

<Impact Resistance Accelerator>

The resin composition of the present invention may contain an impact resistance accelerator. The impact resistance accelerator is not particularly limited as long as it can be used to improve the impact resistance of a thermoplastic resin. For example, at least one selected from the following impact resistance accelerators may be used.

Specific examples of the impact resistance accelerator include ethylene-propylene copolymer, ethylene-propylene-nonconjugated diene copolymer, ethylene-butene-1 copolymer, acrylic rubbers, ethylene-acrylic acid copolymer and alkali metal salts thereof (so-called "ionomers"), ethylene-glycidyl (meth)acrylate copolymer, ethylene-acrylate copolymers (such as ethylene-ethyl acrylate copolymer and ethylene-butyl acrylate copolymer), modified ethylene-propylene copolymer, diene rubbers (such as polybutadiene, polyisoprene and polychloroprene), diene-vinyl copolymers (such as styrene-butadiene random copolymer, styrene-butadiene block copolymer, styrene-butadiene-styrene block copolymer, styrene-isoprene random copolymer, styrene-isoprene block copolymer, styrene-isoprene-styrene block copolymer, polybutadiene-styrene graft copolymer and butadiene-acrylonitrile copolymer), polyisobutylene, copolymer of isobutylene and butadiene or isoprene, natural rubber, Thiokol rubber, polysulfide rubber, polyurethane rubber, polyether rubber and epichlorohydrin rubber.

Further, impact resistance accelerators having different degrees of crosslinking and various micro-structures such as cis-structure and trans-structure, and core-shell type multilayer polymers, each consisting of a core layer and at least one shell layer covering the core layer, or having adjacent layers made of different polymers, may also be used.

Whether the (co)polymers listed above are random copolymers or block copolymers, they may be used as the impact resistance accelerator of the present invention.

The content of the impact resistance accelerator is preferably 1 to 30 parts by weight, more preferably 5 to 20 parts by weight, much more preferably 10 to 20 parts by weight based on 100 parts by weight of the polyester (component A).

<Others>

The resin composition of the present invention may contain a thermosetting resin such as phenol resin, melamine resin, thermocurable polyester resin, silicone resin or epoxy resin in limits not prejudicial to the object of the present invention. The resin composition of the present invention may also contain a flame retardant such as bromine-based, phosphorus-based, silicone-based or antimony compound in limits not prejudicial to the object of the present invention. The resin composition may further contain a colorant including an organic or inorganic dye or pigment, for example, an oxide such as titanium dioxide, a hydroxide such as alumina white, a sulfide such as zinc sulfide, a ferrocyanide compound such as iron blue, a chromate such as zinc chromate, a sulfate such as barium sulfate, a carbonate such as calcium carbonate, a silicate such as ultramarine blue, a phosphate such as manganese violet, carbon such as carbon black, and a metal colorant such as bronze powder or aluminum powder. The resin composition may still further contain additives including nitroso-based condensation polycyclic colorant such as Naphthol Green B, a nitro-based condensation polycyclic colorant such as Naphthol Yellow S, an azo-based condensation polycyclic colorant such as Naphthol Red or Chromophthal Yellow, a phthalocyanine-based condensation polycyclic colorant such as Phthalocyanine Blue or Fast Sky Blue, or Indanthrene Blue, and a slidability accelerator such as graphite or fluororesin. These additives may be used alone or in combination of two or more.

<Molded Article>

A molded article obtained from the resin composition of the present invention can be formed by injection molding, extrusion molding, vacuum or pressure molding or blow molding. Examples of the molded article include a pellet, a fiber, cloth, a fiber structure, a film, a sheet and sheet nonwoven cloth.

The melt molding method of the pellet of the resin composition of the present invention is not limited at all, and pellets produced by known pellet production methods can be advantageously used. That is, methods in which the resin composition extruded into a strand or plate is cut in air or water after the resin is completely solidified or while it is still molten and not completely solidified are conventionally known and preferably used in the present invention.

For injection molding, molding conditions may be suitably set according to the type of the polyester. When the polyester is polylactic acid, the mold temperature is preferably 30° C. or higher, more preferably 60° C. or higher, much more preferably 70° C. or higher in order to promote the crystallization and increase the molding cycle of a molded article at the time of injection molding. However, in order to prevent the deformation of a molded article, the mold temperature is preferably 140° C. or lower, more preferably 120° C. or lower, much more preferably 110° C. or lower.

These molded articles include housings, electric and electronic parts such as gears, construction members, civil engineering members, agricultural materials, auto parts (interior and exterior parts) and parts for daily use.

A fiber and a fiber structure obtained from the resin composition of the present invention by melt spinning and processing after that can be advantageously used.

That is, the polyester (component A) is molten by means of an extruder type or pressure melter type melt extruder, weighed by means of a gear pump, filtered in a pack and ejected from nozzles formed in a spinneret as monofilaments or multifilaments The shape and number of spinnerets are not particularly limited and a circular, atypical, solid or hollow spinneret may be used. The ejected yarn is cooled to be solidified right away, bundled, applied by a lubricant and wound up. The winding rate is not particularly limited but preferably 300 to 5,000 m/min as a stereocomplex crystal is easily formed when the polyester (component A) is stereocomplex polylactic acid.

From the viewpoint of stretchability, the winding rate is preferably a value which ensures that the stereo crystallization ratio (Sc) of unstretched yarn becomes 0%. The wound unstretched yarn is then supplied to the stretching step. The spinning step and the stretching step do not need to be separated from each other, and a direct spinning/stretching method in which stretching is carried out after spinning without winding up the spun yarn may be employed.

Stretching may be carried out in one stage or two or more multiple stages, and the draw ratio is preferably 3 times or more, more preferably 4 times or more, much more preferably 3 to 10 times in order to manufacture a high-strength fiber. The draw ratio is preferably selected from 3 to 10 times. However, when the draw ratio is too high, the fiber is devitrified and whitened, whereby the strength of the fiber is reduced and rupture elongation becomes too small, which is unpreferred for fiber application.

Preheating for stretching may be carried out by increasing the temperature of a roll or using a plate-like or pin-like contact heater, a non-contact hot plate or a heat medium bath. Commonly used means should be used.

After stretching, a heat treatment is preferably carried out at a temperature equal to or higher than the glass transition temperature (Tg) of the polyester (component A) and lower than its melting point before winding. Any means such as a contact type heater or non-contact hot plate may be used for the heat treatment besides a hot roller. The stretching temperature is the glass transition temperature (Tg) to 170° C., preferably 70 to 140° C., particularly preferably 80 to 130° C. when the polyester (component A) is polylactic acid.

When the polyester (component A) is stereocomplex polylactic acid, a polylactic acid fiber having a high stereo crystallization ratio (Sc), low heat shrinkage and a strength of not less than 3.5 cN/dTex can be obtained by heat setting at 170 to 220° C. under tension after stretching.

Fibers obtained from the resin composition may take various fiber structures. Stated more specifically, they include fiber products such as yarn products including sewing yarn, stitch yarn and strings, textiles, knitted goods, fabric including unwoven fabric and felt, outer garments including shirts, jackets, pants, coats, sweaters and uniforms, underwears, panty stockings, socks, liners, interlining cloth, high-value added clothing products including sport clothing, women's clothing and formal wears, clothing products including cups and pads, living material products including curtains, carpets, chair covering, mats, furniture, bags, furniture covering, wall materials, belts and slings, industrial material products including sail cloth, belts, nets, ropes, heavy fabrics, bags, felts and filters, car interior products and artificial leather products.

Fibers and fiber structures comprising the resin composition of the present invention may be obtained from fibers of the resin composition alone or a mixture of the fibers and another type of fibers. Examples of the mixture include a combination of the fibers and a fiber structure made of another type of fibers, combined filament yarn comprising another type of fibers, composite false twisted yarn, blended yarn, long/short composite yarn, fluid processed yarn, covering yarn, twisted yarn, combined weave, combined knitting, pile fabrics, cotton mixing/wadding, long fiber and short fiber mixed nonwoven fabric and felt. When another type of fibers are used together, the mixing ratio of the fibers is preferably not less than 1 wt %, more preferably not less than 10 wt %, much more preferably not less than 30 wt % in order to develop the feature of the polyester (component A).

Examples of the another type of fibers to be mixed include cellulose fibers such as cotton, hemp, rayon and tencel fibers, and wool, silk, acetate, polyester, nylon, acryl, vinylon, polyolefin and polyurethane fibers.

The film and sheet of the present invention are formed by conventionally known methods. For example, the film and sheet are formed by molding techniques such as extrusion molding and cast molding. That is, an unstretched film is extruded by an extruder having a T die or circular die and further stretched and heated to be molded. The unstretched film may be directly used as a sheet. To form a film, a material obtained by melt kneading together the resin composition and the above-described components may be used, or these components may be melt kneaded together at the time of extrusion molding to be molded. An unstretched film having few surface defects can be obtained by mixing an electrostatic adhesive such as quaternary phosphonium sulfonate with the molten resin at the time of extruding an unstretched film.

Further, an unstretched film can also be cast molded by dissolving the resin composition and the additives in a common solvent such as chloroform or methylene dichloride, casting the resulting solution and drying and solidifying it.

The unstretched film may be stretched monoaxially in the mechanical flow direction or in a direction orthogonal to the mechanical flow direction. A biaxially oriented film can be produced by carrying out sequential biaxial stretching with rollers and a tenter, simultaneous biaxial stretching with a tenter or tubular biaxial stretching. Further, the film is generally heat set after stretching to suppress its heat shrinkage. The stretched film obtained as described above may be optionally subjected to a surface activation treatment such as plasma treatment, amine treatment or corona treatment in accordance with a conventionally known method.

The film or sheet of the present invention may be used alone or in combination with another type of a film or sheet. When it is used in combination with another type of a film or sheet, it is assembled with a film or sheet made of another material to obtain, for example, a laminate, or with another form such as an injection molded article or a fiber structure.

EXAMPLES

The following examples are provided to further illustrate the present invention. Characteristic properties were measured by the following methods.

(1) Weight Average Molecular Weight (Mw) and Number Average Molecular Weight (Mn)

The weight average molecular weight and number average molecular weight of a polymer were measured by gel permeation chromatography (GPC) and calculated in terms of standard polystyrene.

GPC measurement was carried out by using the following detector and columns, letting a chloroform eluant flow at a temperature of 40° C. and a flow rate of 1.0 ml/min, and injecting 10 μl of a sample having a concentration of 1 mg/ml (chloroform containing 1% of hexafluoroisopropanol).
Detector: RID-6A differential refractometer of Shimadzu Corporation
Column: TSKgelG3000HXL, TSKgelG4000HXL and TSKgelG5000HXL and TSKguardcokumnHXL-L of Tosoh Corporation are connected in series, or TSKgelG2000HXL, TSKgelG3000HXL and TSKguardcokumnHXL-L are connected in series.
(2) Carboxyl Group Concentration The sample was dissolved in purified o-cresol in a nitrogen gas stream and titrated with an ethanol solution of 0.05 N potassium hydroxide using Bromocresol Blue as an indicator.
(3) DSC Measurement of Stereo Crystal Rate ([S (%)] and Crystal Melting Temperature DSC (TA-2920 of TA Instrument Co., Ltd.) was used to heat the sample up to 250° C. at a temperature elevation rate of 10° C./min in a nitrogen gas stream in a first cycle in order to measure its glass transition temperature (Tg), stereocomplex-phase polylactic acid crystal melting temperature (Tm*), stereocomplex-phase polylactic acid crystal melting enthalpy (ΔHms) and homo-phase polylactic acid crystal meting enthalpy (ΔHmh).

The crystallization start temperature (Tc*) and crystallization temperature (Tc) were measured by quickly cooling the above measurement sample and then carrying out the second cycle measurement under the same conditions. The stereo crystal rate was obtained from the stereocomplex-phase and homo-phase polylactic acid crystal melting enthalpies obtained by the above measurement based on the following equation (ii).

$$S=[\Delta Hms/(\Delta Hmh+\Delta Hms)]\times 100 \quad (ii)$$

(ΔHms is the melting enthalpy of the stereocomplex-phase crystal and ΔHmh is the melting enthalpy of the homo-phase polylactic acid crystal.)
(4) Identification of Cyclic Carbodiimide Structure by NMR and Quantitative Determination of Cyclic Carbodiimide in Polyester Composition The synthesized cyclic carbodiimide compound was confirmed by $^1$H-NMR and $^{13}$C-NMR. The JNR-EX270 of JEOL Ltd. was used for NMR. Heavy chloroform was used as the solvent.
(5) Identification of Carbodiimide Skeleton of Cyclic Carbodiimide by IR The existence of the carbodiimide skeleton of the synthesized cyclic carbodiimide compound at 2,100 to 2,200 cm$^{-1}$ which is the characteristic of a carbodiimide was confirmed by FT-IR. The Magna-750 of Thermonicoley Co., Ltd. was used for FT-IR.
(6) Stability to Hydrolysis The reduced viscosity retention of an aliphatic polyester sample when it was treated at 80° C. and 95% RH for 100 hours in a thermo-hygrostat was evaluated.

The reduced viscosity retention of an aromatic polyester sample when it was treated at 120° C. and 100% RH for 50 hours in a pressure cooker was evaluated.

The hydrolysis stability of the resin composition was evaluated as acceptable when the reduced viscosity retention was 80% or more and less than 90%, as excellent when the reduced viscosity retention was 90% or more and less than 95% and as very excellent when the reduced viscosity retention was 95 to 100%.

The reduced viscosity ($\eta s_{p/c}$) was measured at 35° C. with an Ubbelohde's viscosity metering tube by dissolving 1.2 mg of the sample in 100 ml of a mixed solvent of tetrachloroethane and phenol (6/4), and the reduced viscosity retention was obtained from the reduced viscosity after the treatment of the sample as a numerator and the reduced viscosity before the treatment of the sample as a denominator.
(7) Production of an Isocyanate Smell When a resin composition containing an aromatic polyester was molten at 300° C. for 5 minutes and when a resin composition containing an aliphatic polyester was molten at 260° for 5 minutes, sensory evaluation was made according to whether a measurer detected an isocyanate smell or not. When an isocyanate smell was not detected, the resin composition was judged as acceptable.
(8) Evaluation of Work Environment It was judged whether work environment became worse by an isocyanate small or not at the time of producing a resin composition. When the work environment did not become worse, it was judged as good.
(9) Qualitative and Quantitative Evaluation of Production of Isocyanate Gas The sample was heated at 260° C. for 8 minutes to carry out the qualitative and quantitative determination of an isocyanate gas by thermal decomposition GC/MS analysis. The quantitative determination was made by using an analytical curve formed with an isocyanate. GC/MS Jms Q1000GC K9 of JEOL Ltd. was used for GC/MS.

The compounds used in the present invention are described below. The following compounds were produced and used as the cyclic carbodiimide compound.

Production Example 1

Cyclic Carbodiimide CC1

CC1: MW=252

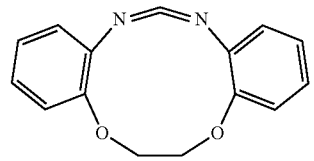 [SMILES: C1=Nc2ccccc2OCCOc2ccccc2N=1]

O-nitrophenol (0.11 mol), 1,2-dibromoethane (0.05 mol), potassium carbonate (0.33 mol) and 200 ml of N,N-dimethylformamide (DMF) were fed to a reactor equipped with a stirrer and a heater in an N$_2$ atmosphere and reacted at 130° C. for 12 hours, DMF was removed under reduced pressure, the obtained solid was dissolved in 200 ml of dichloromethane, and the resulting solution was separated with 100 ml of water 3 times. An organic layer was dehydrated with 5 g of sodium sulfate and dichloromethane was removed under reduced pressure to obtain an intermediate product A (nitro compound).

Then, the intermediate product A (0.1 mol), 5% palladium carbon (Pd/C) (1 g) and 200 ml of ethanol/dichloromethane (70/30) were fed to a reactor equipped with a stirrer, hydrogen substitution was carried out 5 times, and a reaction was carried out while hydrogen was always supplied at 25° C. and terminated when the amount of hydrogen did not decrease any more. When Pd/C was collected and the mixed solvent was removed, an intermediate product B (amine compound) was obtained.

Then, triphenylphosphine dibromide (0.11 mol) and 150 ml of 1,2-dichloroethane were fed to a reactor equipped with a stirrer, a heater and a dropping funnel in an N$_2$ atmosphere and stirred. A solution obtained by dissolving the intermediate product B (0.05 mol) and triethylamine (0.25 mol) in 50 ml of 1,2-dichloroethane was gradually added dropwise to the resulting mixture at 25° C. After the end of addition, a reaction was carried out at 70° C. for 5 hours. Thereafter, the reaction solution was filtered, and the filtrate was separated with 100 ml of water 5 times. An organic layer was dehydrated with 5 g of sodium sulfate and 1,2-dichloroethane was removed under reduced pressure to obtain an intermediate product C (triphenylphosphine compound).

Thereafter, di-tert-butyl dicarbonate (0.11 mol), N,N-dimethyl-4-aminopyridine (0.055 mol) and 150 ml of dichloromethane were fed to a reactor equipped with a stirrer and a dropping funnel in an $N_2$ atmosphere and stirred. 100 ml of dichloromethane containing the intermediate product C (0.05 mol) dissolved therein was gradually added dropwise to the resulting mixture at 25° C. After the end of addition, a reaction was carried out for 12 hours. Thereafter, a solid obtained by removing dichloromethane was purified to obtain CC1. The structure of CC1 was checked by NMR and IR.

Production Example 2

Cyclic Carbodiimide CC2

CC2: MW=516

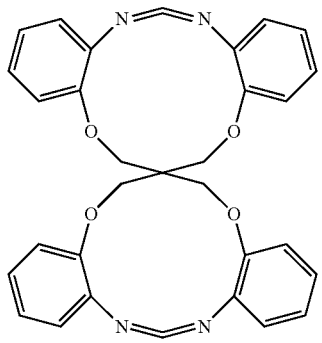 [SMILES: C1=Nc2ccccc2OCC2(COc3ccccc3N=1)COc1ccccc1N=C=Nc1ccccc1OC2]

o-nitrophenol (0.11 mol), pentaerythritol tetrabromide (0.025 mol), potassium carbonate (0.33 mol) and 200 ml of N,N-dimethylformamide were fed to a reactor equipped with a stirrer and a heater in an $N_2$ atmosphere and reacted at 130° C. for 12 hours, DMF was removed under reduced pressure, the obtained solid was dissolved in 200 ml of dichloromethane, and the resulting solution was separated with 100 ml of water 3 times. An organic layer was dehydrated with 5 g of sodium sulfate and dichloromethane was removed under reduced pressure to obtain an intermediate product D (nitro compound).

Then, the intermediate product D (0.1 mol), 5% palladium carbon (Pd/C) (2 g) and 400 ml of ethanol/dichloromethane (70/30) were fed to a reactor equipped with a stirrer, hydrogen substitution was carried out 5 times, and a reaction was carried out while hydrogen was always supplied at 25° C. and terminated when the amount of hydrogen did not decrease any more. When Pd/C was collected and the mixed solvent was removed, an intermediate product E (amine compound) was obtained.

Then, triphenylphosphine dibromide (0.11 mol) and 150 ml of 1,2-dichloroethane were fed to a reactor equipped with a stirrer, a heater and a dropping funnel in an $N_2$ atmosphere and stirred. A solution obtained by dissolving the intermediate product E (0.025 mol) and triethylamine (0.25 mol) in 50 ml of 1,2-dichloroethane was gradually added dropwise to the resulting mixture at 25° C. After the end of addition, a reaction was carried out at 70° C. for 5 hours. Thereafter, the reaction solution was filtered, and the filtrate was separated with 100 ml of water 5 times. An organic layer was dehydrated with 5 g of sodium sulfate and 1,2-dichloroethane was removed under reduced pressure to obtain an intermediate product F (triphenylphosphine compound).

Thereafter, di-tert-butyl dicarbonate (0.11 mol), N,N-dimethyl-4-aminopyridine (0.055 mol) and 150 ml of dichloromethane were fed to a reactor equipped with a stirrer and a dropping funnel in an $N_2$ atmosphere and stirred. 100 ml of dichloromethane containing the intermediate product F (0.025 mol) dissolved therein was gradually added dropwise to the resulting mixture at 25° C. After the end of addition, a reaction was carried out for 12 hours. A solid obtained by removing dichloromethane was purified to obtain CC2. The structure of CC2 was confirmed by NMR and IR.

The following polyesters were used.
(1) Polyester (A1): Aromatic Polyester

The TR-8580 polyethylene terephthalate (PET) of Teijin Fiber Co., Ltd. was used. Its reduced viscosity was 0.35 dl/g. The results of its carboxyl group concentration and stability to hydrolysis are shown in Table 1.
(2) Polyester (A2): Aromatic Polyester Polybutylene terephthalate (PBT) (melting point of 227° C., viscosity average molecular weight of 38,000, Tg of 66° C.) manufactured by Aldrich Co., Ltd. was used. Its reduced viscosity was 1.21 dl/g. The results of its carboxyl group concentration and stability to hydrolysis are shown in Table 1.
(3) Polyester (A3): Aliphatic Polyester 0.005 part by weight of tin octylate was added to 100 parts by weight of L-lactide (manufactured by Musashino Kagaku Kenkyuusho Co., Ltd., optical purity of 100%) to carry out a reaction at 180° C. in a reactor quipped with a stirring blade in a nitrogen atmosphere for 2 hours, phosphoric acid was added as a catalyst deactivator in an amount of 1.2 times the equivalent of tin octylate, the residual lactide was removed at 13.3 Pa, and the residue was formed into a chip to obtain poly(L-lactic acid) (PLLA). The obtained poly(L-lactic acid) had a weight average molecular weight of 152,000, a glass transition temperature (Tg) of 55° C. and a melting point of 175° C. The results of its carboxyl group concentration and stability to hydrolysis are shown in Table 1.
(4) Polyester (A4): Aliphatic Polyester Poly(D-lactic acid) (PDLA) was obtained by carrying out polymerization under the same conditions as in the production of the above polyester (A3) except that L-lactide was changed to D-lactide (manufactured by Musashino Kagaku Kenkyuusho Co., Ltd., optical purity of 100%). The obtained poly(D-lactic acid) had a weight average molecular weight of 151,000, a glass transition temperature (Tg) of 55° C. and a melting point of 175° C. The results of its carboxyl group concentration and stability to hydrolysis are shown in Table 1.

Example 1

Resin Composition Comprising CC2

After 100 parts by weight of the polyester (A3) was vacuum dried at 110° C. for 5 hours, supplied from the first feed port of a double-screw kneader and melt kneaded at a cylinder temperature of 210° C. while vacuum evacuation was carried out at a vent pressure of 13.3 Pa, 1 part by weight of the cyclic carbodiimide (CC2) was supplied from the second feed port and melt kneaded with the above polyester at a cylinder temperature of 210° C., and the resulting product was extruded into a strand in a water tank and cut into a chip with a chip cutter to obtain a composition (M1) having a crystal melting temperature measured by DSC of 175° C. An isocyanate smell was not detected during the production of the composition. When the composition was molten at 260° C. for 5 minutes, an isocyanate smell was evaluated as acceptable. The results of the carboxyl group concentration and stability to hydrolysis of this composition are shown in Table 1.

Example 2

Resin Composition Comprising CC1

After 100 parts by weight of the polyester (A4) in place of the polyester (A3) in Example 1, 0.3 part by weight of a phosphate metal salt (Adecastab NA-11 of ADEKA Corporation) as a crystal nucleating agent and 0.5 part by weight of the Micro Ace P-6 particulate talc (MAP6 of Nippon Talc Co., Ltd.) were mixed together by means of a blender and vacuum dried at 110° C. for 5 hours, the resulting mixture was supplied from the first feed port of a double-screw kneader and melt kneaded at a cylinder temperature of 210° C. while vacuum evacuation was carried out at a vent pressure of 13.3 Pa, 1 part by weight of the cyclic carbodiimide (CC1) was supplied from the second feed port and melt kneaded with the above mixture at a cylinder temperature of 210° C., and the resulting product was extruded into a strand in a water tank and cut into a chip with a chip cutter to obtain a composition (M2) having a crystal melting temperature measured by DSC of 175° C.

An isocyanate smell was not detected during the production of the composition. When the composition was molten at 260° C. for 5 minutes, an isocyanate smell was evaluated as acceptable. The results of the carboxyl group concentration and stability to hydrolysis of this composition are shown in Table 1.

Comparative Example 1

Resin Composition Comprising Linear Polycarbodiimide (LA-1)

A composition (M7) having a crystal melting temperature measured by DSC of 174° C. was obtained in the same manner as in Example 1 except that the carbodiimide compound was changed to linear carbodiimide LA-1 (Carbodilite LA-1 of Nisshinbo Industries, Inc.). A strong isocyanate smell was detected during the production of the composition and the work environment was judged as bad. When the composition was molten at 260° C. for 5 minutes, an isocyanate smell was evaluated as unacceptable. The results of the carboxyl group concentration and stability to hydrolysis of this composition are shown in Table 1.

Example 3

Resin Composition Comprising CC2

After 50 parts by weight of the polyester (A3), 50 parts by weight of the polyester (A4) and 0.3 part by weight of a phosphate metal salt (Adecastab NA-11 of ADEKA Corporation) were mixed together by means of a blender, vacuum dried at 110° C. for 5 hours, supplied from the first feed port of a kneader and melt kneaded at a cylinder temperature of 230° C. while vacuum evacuation was carried out at a vent pressure of 13.3 Pa, 1 part by weight of the cyclic carbodiimide (CC2) was supplied from the second feed port and melt kneaded with the above mixture at a cylinder temperature of 230° C., and the resulting product was extruded into a strand in a water tank and cut into a chip with a chip cutter to obtain a composition (M3) having a stereo crystal rate (S) of 100% and a crystal melting temperature of 216° C. The work environment was kept good without detecting an isocyanate smell during the production of the composition. When the composition was molten at 260° C. for 5 minutes, an isocyanate smell was evaluated as acceptable. The results of the carboxyl group concentration and stability to hydrolysis of this composition are shown in Table 1. When the amount of an isocyanate gas produced from this composition was measured by GC/MS, no isocyanate gas was detected.

Example 4

Resin Composition Comprising CC1

A composition (M4) having a stereo crystal rate (S) of 99% and a crystal melting temperature of 215° C. was obtained in the same manner as in Example 3 except that the cyclic carbodiimide (CC1) was used. The work environment was kept good without detecting an isocyanate smell during the production of the composition. When the composition was molten at 260° C. for 5 minutes, an isocyanate smell was evaluated as acceptable. The results of the carboxyl group concentration and stability to hydrolysis of this composition are shown in Table 1.

When the content of the cyclic carbodiimide (CC1) in the composition was checked by NMR, it was 0.6 part by weight based on 100 parts by weight of the composition. When the amount of an isocyanate gas produced from this composition was measured by GC/MS, no isocyanate gas was detected.

Comparative Example 2

Cyclic Carbodiimide-free Resin

The procedure of Example 3 was repeated to obtain a resin (M8) having a stereo crystal rate (S) of 100% and a crystal melting temperature of 217° C. except that the cyclic carbodiimide (CC2) was not supplied. The results of the carboxyl group concentration and stability to hydrolysis of this composition are shown in Table 1.

Comparative Example 3

Resin Composition Comprising Linear Carbodiimide (Sb-I)

A composition (M9) having a stereo crystal rate (S) of 100% and a crystal melting temperature of 215° C. was obtained in the same manner as in Example 3 except that the carbodiimide compound was changed to linear carbodiimide Sb-I (Stabacsol I of Line Chemie Japan Co., Ltd.). A strong isocyanate smell was detected during the production of this composition and an air exhauster must have been installed. When the composition was molten at 260° C. for 5 minutes, an isocyanate smell was evaluated as unacceptable. The results of the carboxyl group concentration and stability to hydrolysis of this composition are shown in Table 1.

Comparative Example 4

Resin Composition Comprising Linear Carbodiimide (LA-1)

A composition (M10) having a stereo crystal rate (S) of 98 and a crystal melting temperature of 213° C. was obtained in the same manner as in Example 3 except that the carbodiimide compound was changed to linear carbodiimide LA-1 (Carbodilite LA-1 of Nisshinbo Industries, Inc.). A strong isocyanate smell was detected during the production of this composition and an air exhauster must have been installed. When the composition was molten at 260° C. for 5 minutes, an isocyanate smell was evaluated as unacceptable. The results of the carboxyl group concentration and stability to hydrolysis of this composition are shown in Table 1. When the amount of an isocyanate gas produced from this composition was measured by GC/MS, 430 ppm of an isocyanate derived from LA-1 was detected.

Example 5

Resin Composition Comprising CC2

After 100 parts by weight of the polyester (A1) was vacuum dried at 110° C. for 5 hours, supplied from the first feed port of a double-screw kneader and melt kneaded at a cylinder temperature of 270° C. while vacuum evacuation was carried out at a vent pressure of 13.3 Pa, 1.5 parts by weight of the cyclic carbodiimide (CC2) was supplied from the second feed port, melt kneaded with the above polyester at a cylinder temperature of 270° C., and the resulting product was extruded into a strand in a water tank and cut into a chip with a chip cutter to obtain a composition (M5). An isocyanate smell was not detected during the production of the composition. When the composition was molten at 300° C. for 5 minutes, an isocyanate smell was evaluated as acceptable. The results of the carboxyl group concentration and stability to hydrolysis of this composition are shown in Table 1.

Comparative Example 5

Resin Composition Comprising Linear Carbodiimide (LA-1)

A composition (M11) was obtained in the same manner as in Example 5 except that the carbodiimide compound was changed to linear carbodiimide LA-1 (Carbodilite LA-1 of Nisshinbo Industries, Inc.). A strong isocyanate smell was detected during the production of this composition and an air exhauster must have been installed. When the composition was molten at 300° C. for 5 minutes, an isocyanate smell was evaluated as unacceptable. The results of the carboxyl group concentration and stability to hydrolysis of this composition are shown in Table 1.

Example 6

Resin Composition Comprising CC2

After 100 parts by weight of the polyester (A2) was vacuum dried at 110° C. for 5 hours, supplied from the first feed port of a double-screw kneader and melt kneaded at a cylinder temperature of 270° C. while vacuum evacuation was carried out at a vent pressure of 13.3 Pa, 2 parts by weight of the cyclic carbodiimide (CC2) was supplied from the second feed port and melt kneaded with the above polyester at a cylinder temperature of 270° C., and the resulting product was extruded into a strand in a water tank and cut into a chip with a chip cutter to obtain a composition (M6). An isocyanate smell was not detected during the production of the composition. When the composition was molten at 300° C. for 5 minutes, an isocyanate smell was evaluated as acceptable. The results of the carboxyl group concentration and stability to hydrolysis of this composition are shown in Table 1.

TABLE 1

| | | | | | | Ex. 1 | Ex. 2 | Ex. 3 | Ex. 4 | Ex. 5 |
|---|---|---|---|---|---|---|---|---|---|---|
| Polyester/resin composition | symbol | A1 | A2 | A3 | A4 | M1 | M2 | M3 | M4 | M5 |
| Polyester | type | PET | PBT | PLLA | PDLA | PLLA | PDLA | PLLA50 wt % PDLA50 wt % | PLLA50 wt % PDLA50 wt % | PET |
| Carbodiimide | type | — | — | — | — | CC2 | CC1 | CC2 | CC1 | CC2 |
| | wt % | — | — | — | — | 1 | 1 | 1 | 1 | 1.5 |
| Crystal nucleating agent | type | — | — | — | — | — | NA-11 | NA-11 | NA-11 | — |
| | wt % | — | — | — | — | — | 0.3 | 0.3 | 0.3 | — |
| Carboxyl group concentration | eq/ton | 31 | 50 | 14 | 15 | 0.5 | 0.8 | 0.4 | 0.7 | 1.2 |
| Stereo crystal rate (S) | % | — | — | — | — | — | — | 100 | 99 | — |
| Reduced viscosity retention | % | 71.8 | 85.1 | 9.5 | 9.1 | 98 | 96.5 | 100 | 97 | 93 |
| Work environment | | — | — | — | — | good | good | good | good | good |

| | | Ex. 6 | C. Ex. 1 | C. Ex. 2 | C. Ex. 3 | C. Ex. 4 | C. Ex. 5 |
|---|---|---|---|---|---|---|---|
| Polyester/resin composition | symbol | M6 | M7 | M8 | M9 | M10 | M11 |
| Polyester | type | PBT | PLLA | PLLA50 wt % PDLA50 wt % | PLLA50 wt % PDLA50 wt % | PLLA50 wt % PDLA50 wt % | PET |
| Carbodiimide | type | CC2 | LA-1 | — | Sb-1 | LA-1 | LA-1 |
| | wt % | 2 | 1 | — | 1 | 1 | 1.5 |
| Crystal nucleating agent | type | — | — | NA-11 | NA-11 | NA-11 | — |
| | wt % | — | — | 0.3 | 0.3 | 0.3 | — |
| Carboxyl group concentration | Eq/ton | 2.1 | 0.5 | 11.3 | 0.7 | 0.5 | 1.5 |
| Stereo crystal rate (S) | % | — | — | 100 | 100 | 98 | — |
| Reduced viscosity retention | % | 96 | 98 | 10 | 95 | 98 | 92 |
| Work environment | | good | Bad | good | Bad | Bad | Bad |

Ex.: Example
C. Ex.: Comparative Example

Effect of the Invention

According to the present invention, an end of a polyester can be sealed with a cyclic carbodiimide compound without liberating an isocyanate compound. As a result, the production of a bad smell from a free isocyanate compound can be suppressed and work environment can be improved.

When an end of a polyester is sealed with a cyclic carbodiimide compound, an isocyanate group is formed at the end of the polyester and the molecular weight of the polyester can be increased by the reaction of the isocyanate group. The cyclic carbodiimide compound also has the function of capturing a free monomer and a compound having an acid group in the polyester. Further, according to the present invention, since the cyclic carbodiimide compound has a Cyclic structure, it can seal an end under a more mild condition as compared with a linear carbodiimide compound.

The difference between a linear carbodiimide compound and a cyclic carbodiimide compound in the end-sealing reaction mechanism is described below.

When the linear carbodiimide compound ($R_1$—N=C=N—$R_2$) is used as an end-sealing agent for a polyester having a terminal carboxyl group, a reaction represented by the following formula takes place. In the formula, W is the main chain of the polyester. An amide group is formed at an end of the polyester through a reaction between the linear carbodiimide compound and the carboxyl group, and an isocyanate compound ($R_1$NCO) is liberated.

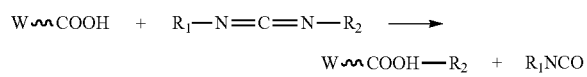

Meanwhile, when the cyclic carbodiimide compound is used as an end-sealing agent for a polyester having a terminal carboxyl group, a reaction represented by the following formula takes place. It is understood that an isocyanate group (—NCO) is formed at an end of the polyester via an amide group through a reaction between the cyclic carbodiimide compound and the carboxyl group and that an isocyanate compound is not liberated.

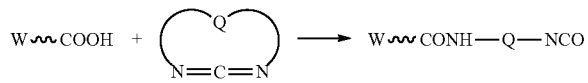

(in the above formula, Q is a divalent to tetravalent bond group which is selected from an aliphatic group, an alicyclic group, an aromatic group or a combination of these and may contain a heteroatom or a substituent.)

Industrial Applicability

The resin composition of the present invention is useful as a raw material for various molded articles.

The invention claimed is:

1. A resin composition comprising a polyester (component A) and a compound including a cyclic structure having only one carbodiimide whose first nitrogen and second nitrogen are bonded together by a bond group in the cyclic structure (component B),
   wherein the number of atoms forming the cyclic structure of the component B is 8 to 50, and
   wherein the component B is represented by the following formula (4):

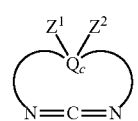

(4)

wherein $Q_c$ is a tetravalent bond group which is selected from an aliphatic group, an alicyclic group, an aromatic group or a combination of these and may contain a heteroatom, and $Z^1$ and $Z^2$ are each a carrier supporting the cyclic structure, wherein $Z^1$ and $Z^2$ may be bonded together to form a cyclic structure, or wherein $Z^1$ and $Z^2$ may each be a bond part, and a plurality of cyclic structures may be bonded together by $Z^1$ and $Z^2$.

2. The resin composition according to claim 1, wherein $Q_c$ is a tetravalent bond group represented by the following formula (4-1), (4-2) or (4-3):

 (4-1)

 (4-2)

 (4-3)

wherein $Ar_c^1$ and $Ar_c^2$ are each independently a divalent to tetravalent aromatic group having 5 to 15 carbon atoms and may contain a heteroatom or a substituent, $R_c^1$ and $R_c^2$ are each independently a divalent to tetravalent aliphatic group having 1 to 20 carbon atoms, a divalent to tetravalent alicyclic group having 3 to 20 carbon atoms, a combination thereof, or a combination of the aliphatic group, the alicyclic group and a divalent to tetravalent aromatic group having 5 to 15 carbon atoms, and may contain a heteroatom or a substituent, $X_c^1$ and $X_c^2$ are each independently a divalent to tetravalent aliphatic group having 1 to 20 carbon atoms, a divalent to tetravalent alicyclic group having 3 to 20 carbon atoms, a divalent to tetravalent aromatic group having 5 to 15 carbon atoms, or a combination thereof, and may contain a heteroatom or a substituent, s is an integer of 0 to 10, k is an integer of 0 to 10, with the proviso that when s or k is 2 or more, $X_c^1$ or $X_c^2$ as a recurring unit may differ from another $X_c^1$ or $X_c^2$, respectively, $X_c^3$ is a divalent to tetravalent aliphatic group having 1 to 20 carbon atoms, a divalent to tetravalent alicyclic group having 3 to 20 carbon atoms, a divalent to tetravalent aromatic group having 5 to 15 carbon atoms, or a combination thereof, and may contain a heteroatom or a substituent, with the proviso that one of $Ar_c^1$, $Ar_c^2$, $R_c^1$, $R_c^2$, $X_c^1$, $X_c^2$ and $X_c^3$ is a tetravalent group, or two of them are tervalent groups.

3. The resin composition according to claim 1, wherein $Z^1$ and $Z^2$ are each independently a single bond, a double bond, an atom, an atom group or a polymer.

4. The resin composition according to claim 1, wherein the compound including a cyclic structure is a compound represented by the following formula (4-1-1):

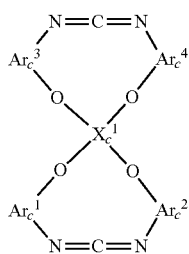

(4-1-1)

wherein $X_c^1$ is an alkanetetrayl group having 1 to 20 carbon atoms, and $Ar_c^1$, $Ar_c^2$, $Ar_c^3$ and $Ar_c^4$ are each independently an arylene group having 5 to 15 carbon atoms which may be substituted.

5. The resin composition according to claim 2, wherein the compound including a cyclic structure is a compound represented by the following formula (4-1-1c):

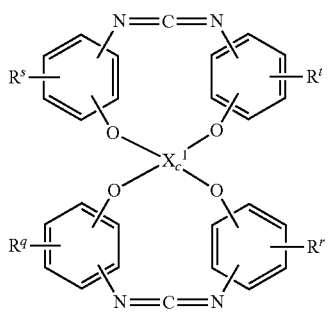

(4-1-1c)

wherein $X_c^1$ is an alkanetetrayl group having 1 to 20 carbon atoms, and $R^q$, $R^r$, $R^s$ and $R^t$ are each independently a hydrogen atom or an alkyl group having 1 to 20 carbon atoms.

6. The resin composition according to claim 1, wherein the main chain of the polyester (component A) is essentially composed of a lactic acid unit represented by the following formula (I) and at least part of an end of the polyester is sealed with the component B:

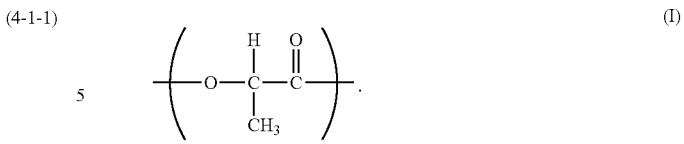

(I)

7. The resin composition according to claim 6, wherein the main chain of the polyester (component A) is essentially composed of an L-lactic acid unit, a D-lactic acid unit or a combination thereof.

8. The resin composition according to claim 6, wherein the polyester (component A) has a stereocomplex phase formed by poly(L-lactic acid) and poly(D-lactic acid).

9. The resin composition according to claim 6 which has a crystal melting peak at 190° C. or higher in differential scanning calorimeter (DSC) measurement.

10. The resin composition according to claim 6 which has a stereo crystal rate (S) defined by the following equation (i) of 90 to 100%:

$$S=[\Delta Hms/(\Delta Hmh+\Delta Hms)]\times 100 \qquad (i)$$

wherein ΔHms is the crystal melting enthalpy of the stereocomplex-phase polylactic acid and ΔHmh is the melting enthalpy of the homo-phase crystal of polylactic acid.

11. The resin composition according to claim 1, wherein the content of the component B is 0.001 to 10 parts by weight based on 100 parts by weight of the polyester (component A).

12. A molded article of the resin composition of claim 1.

13. A process for producing a resin composition of claim 1, comprising melt kneading a polyester (component A) with a compound including a cyclic structure having only one carbodiimide group whose first nitrogen and second nitrogen are bonded together by a bond group in the cyclic structure (component B).

14. The production process according to claim 13, wherein the component B is melt kneaded in an amount corresponding to 0.5 to 100 equivalents of a carbodiimide group based on 1 equivalent of the carboxyl group of the polyester (component A).

* * * * *